(12) United States Patent
deJong et al.

(10) Patent No.: US 6,936,469 B2
(45) Date of Patent: Aug. 30, 2005

(54) METHODS FOR DELIVERING NUCLEIC ACID MOLECULES INTO CELLS AND ASSESSMENT THEREOF

(75) Inventors: Gary deJong, North Vancouver (CA); Sandra Louise Vanderbyl, Burnaby (CA)

(73) Assignee: Chromos Molecular Systems Inc. (CA)

(*) Notice: Subject to any disclaimer, the term of this patent is extended or adjusted under 35 U.S.C. 154(b) by 16 days.

(21) Appl. No.: 09/815,981

(22) Filed: Mar. 22, 2001

(65) Prior Publication Data

US 2003/0003435 A1 Jan. 2, 2003

(51) Int. Cl.[7] .................... C12N 15/88; C12N 15/63; C12N 15/82; C12Q 1/68; C12Q 1/66
(52) U.S. Cl. .................. 435/458; 435/455; 435/468; 435/6; 435/8; 435/19; 435/21
(58) Field of Search .................. 435/455, 458, 435/468, 6, 8, 19, 21

(56) References Cited

U.S. PATENT DOCUMENTS

| | | | | |
|---|---|---|---|---|
| 4,897,355 A | * | 1/1990 | Eppstein et al. | |
| 4,937,190 A | | 6/1990 | Palmenberg et al. | 435/69.1 |
| 5,208,066 A | | 5/1993 | Fujisaki et al. | 427/96 |
| 5,288,625 A | | 2/1994 | Hadlaczky | 435/172.2 |
| 5,318,515 A | | 6/1994 | Wilk | 604/30 |
| 5,334,761 A | | 8/1994 | Gebeyehu et al. | 564/197 |
| 5,389,069 A | | 2/1995 | Weaver | 604/21 |
| 5,459,127 A | * | 10/1995 | Felgner et al. | |
| 5,501,662 A | | 3/1996 | Hofmann | 604/20 |
| 5,507,724 A | | 4/1996 | Hofmann et al. | 604/53 |
| 5,550,289 A | | 8/1996 | Eppstein et al. | 564/293 |
| 5,676,151 A | | 10/1997 | Yock | 128/662.06 |
| 5,695,967 A | | 12/1997 | Van Bokkelen et al. | 435/91.1 |
| 5,712,134 A | | 1/1998 | Hadlaczky | 435/172.2 |
| 5,721,118 A | | 2/1998 | Scheffler | 435/69.1 |
| 5,736,392 A | | 4/1998 | Hawley-Nelson et al. | 435/320.1 |
| 5,747,338 A | * | 5/1998 | Giese et al. | 435/348 |
| 5,830,430 A | | 11/1998 | Unger et al. | 424/1.21 |
| 5,837,283 A | | 11/1998 | McDonald et al. | 424/450 |
| 5,843,884 A | | 12/1998 | Sims | 514/2 |
| 5,853,694 A | | 12/1998 | Engberts et al. | 424/1.21 |
| 5,869,294 A | | 2/1999 | Harrington et al. | 435/91.1 |
| 5,891,691 A | | 4/1999 | Hadlaczky | 435/172.3 |
| 5,944,710 A | | 8/1999 | Dev et al. | 604/500 |
| 5,962,265 A | | 10/1999 | Norris et al. | 435/69.1 |
| 5,965,396 A | | 10/1999 | Pan et al. | 435/69.1 |
| 5,976,796 A | | 11/1999 | Szalay et al. | 435/6 |
| 5,976,849 A | | 11/1999 | Hustad et al. | 435/183 |
| 5,985,577 A | | 11/1999 | Bulinski | 435/6 |
| 5,993,434 A | | 11/1999 | Dev et al. | 604/501 |
| 6,025,155 A | | 2/2000 | Hadlaczky et al. | 435/69.1 |
| 6,027,488 A | | 2/2000 | Hofmann et al. | 604/522 |
| 6,034,228 A | | 3/2000 | Norris et al. | 536/23.1 |
| 6,037,133 A | | 3/2000 | Li | 435/7.21 |
| 6,054,312 A | | 4/2000 | Larocca et al. | 435/320.1 |
| 6,074,667 A | | 6/2000 | Kinnunen et al. | 424/450 |
| 6,077,697 A | | 6/2000 | Hadlaczky et al. | 435/172.3 |
| 6,184,037 B1 | | 2/2001 | Rolland et al. | 435/455 |
| 6,743,967 B2 | * | 6/2004 | Hadlaczky et al. | 800/25 |
| 2002/0160410 A1 | * | 10/2002 | Hadlaczky et al. | 435/6 |
| 2002/0160970 A1 | * | 10/2002 | Hadlaczky et al. | 514/44 |
| 2003/0033617 A1 | * | 2/2003 | Hadlaczky et al. | 800/6 |
| 2003/0059940 A1 | * | 3/2003 | de Jong et al. | 435/455 |
| 2003/0083293 A1 | * | 5/2003 | Hadlaczky et al. | 514/44 |
| 2003/0101480 A1 | * | 5/2003 | Hadlaczky et al. | 800/278 |
| 2003/0108914 A1 | * | 6/2003 | Hadlaczky | 435/6 |
| 2003/0113917 A1 | * | 6/2003 | de Jong et al. | 435/455 |
| 2003/0119104 A1 | * | 6/2003 | Perkins et al. | 435/69.1 |
| 2003/0186390 A1 | * | 10/2003 | de Jong et al. | 435/91.1 |
| 2003/0224522 A1 | * | 12/2003 | de Jong et al. | 435/458 |
| 2004/0214290 A1 | * | 10/2004 | Perez et al. | 435/91.1 |

FOREIGN PATENT DOCUMENTS

| | | |
|---|---|---|
| EP | 0755924 | 1/1997 |
| EP | 0755924 | 6/1999 |
| WO | 9740183 | 10/1997 |
| WO | 9808964 | 3/1998 |
| WO | WO 99/13719 | * 3/1999 |
| WO | 9921584 | 5/1999 |
| WO | 99/54445 | 10/1999 |
| WO | WO 0034436 | * 6/2000 |

OTHER PUBLICATIONS

Zelphati et al. Gene chemistry: functionally and conformationally intact fluorescent plasmid DNA. Hum Gene Ther. Jan. 1, 1999;10(1):15–24.*

Neves et al. Novel method for covalent fluorescent labeling of plasmid DNA that maintains structural integrity of the plasmid. Bioconjug Chem. Jan.–Feb. 2000;11(1):51–5.*

Lee and Jaenisch, "A method for high efficiency YAC lipofection into murine embryonic stem cells", Nucleic Acids Res. 24(24):5054–5055 (1996).

Monteith DP, Leung JD, Borowski AH, Co DO, Praznovszky T, Jirik FR, Hadlaczky G, Perez CF, "Pronuclear microinjection of purified artificial chromosomes for generation of transgenic mice: pick–and–inject technique," Method Mol. Biol. 240:227–42 (2004).

(Continued)

*Primary Examiner*—David Guzo
*Assistant Examiner*—Daniel M. Sullivan
(74) *Attorney, Agent, or Firm*—Fish & Richardson P.C.; Stephanie Seidman

(57) ABSTRACT

Methods for delivering nucleic acid molecules into cells and methods for measuring nucleic acid delivery into cells and the expression of the nucleic acids are provided. The methods are designed for introduction of large nucleic acid molecules, including artificial chromosomes, into cells, and are practiced in vitro and in vivo.

18 Claims, No Drawings

OTHER PUBLICATIONS

Lindenbaum M, Perkins E, Csonka E, Fleming E, Garcia L, Greene A, Gung L, Hadlaczky G, Lee E, Leung J, MacDonald N, Maxwell A, Mills K, Monteith D, Perez CF, Shellard J, Stewart S, Stodola T, Vandenborre D, Vanderbyl S, Ledebur HC Jr., "A mammalian artificial chromosome engineering system (ACE System) applicable to biopharmaceutical protein production, transgenesis and gene–based cell therapy", *Nucleic Acids Res.* Dec 07;32(21):e172 (2004).

Perez, CF, Vanderbly SL, Mills KA, Ledebur HC, "The ACE System: A versatile chromosome engineering technology with applications for gene–based cell therapy", BioProcessing 2004; 3:61–68.

Rech et al., "Introduction of a yeast artificial chromosome vector into *Saccharomyces cereviseae* cells by electroporation", Nucleic Acids Res. 18(5):1313 (1990).

Tseng et al., "Mitosis enhances transgene expression of plasmid delivered by cationic liposomes", Biochemica et Biophysica Acta 1445:53–64 (1999).

Vanderbyl S, MacDonald GN, Sidhu S, Gung L, Telenius A, Perez C, Perkins E, "Transfer and stable transgene expression of a mammalian artificial chromosome into bone marrow–derived human mesenchymal stem cells", Stem Cells 22(3):324–33 (2004).

Albertsen et al., "Construction and characterization of a yeast artificial chromosome library containing seven haploid human genome equivalents", *PNAS*, 87:4256–4260 (1990).

Alvaro–Gracia et al., "Cytokines in Chronic Inflammatory Arthritis. V. Mutual Antagonism between Interferon–Gamma and Tumor Necrosis Factor–Alpha on HLA–DR Expression, Proliferation, Collagenase Production, and Granulocyte Macrophage Colony–stimulating Factor Production by Rheumatoid Arthritis Synoviocytes", *J. Clin. Invest.,* 86:1790–1798 (1990).

Aupperle et al., "NF–κB Regulation by IκB Kinase in Primary Fibroblast–Like Synoviocytes", *J. Immunol.,* 163:427–433 (1999).

Brown et al., "Artificial chromosomes: ideal vectors?", *TIBTech,* 18:218–223 (2000).

Cavazzana–Calvo et al., "Gene Therapy of Human Severe Combined Immunodeficiency (SCID)–X1 Disease", *Science,* 288:669–672 (2000).

Cocchia et al., "Recovery and potential utility of YACs as circular YACs/BACs", *Nucl. Acids Res.,* 28(17):e81 i–viii (2000).

Dausset et al., "The CEPH YAC Library", *Behring Inst. Mitt.,* 91:13–20 (1992).

de Jong et al., "Efficient in–vitro transfer of a 60–Mb mammalian artificial chromosome into murine and hamster cells using cationic lipids and dendrimers", *Chromosome Res.,* 9:475–485 (2001).

Foecking et al., "Powerful and versatile enhancer–promoter unit for mammalian expression vectors", *Gene,* 45:101–105 (1986).

Giraldo et al., "Size matters: use of YACs, BACs and PACs in transgenic animals", *Transgenic Res.,* 10:83–103 (2001).

Han et al., "Development of Biomaterials for Gene Therapy", *Mol. Therapy,* 2(4):302–317 (2000).

Hem et al., "Saphenous vein puncture for blood sampling of the mouse, rat, hamster, gerbil, guineapig, ferret and mink", *Laboratory Animals,* 32:364–368 (1998).

Jacobovits et al., "Germ–line transmission and expression of a human–derived yeast artificial chromosome", *Nature,* 362:255–258 (1993).

Kong et al., "Activated T cells regulate bone loss and joint destruction in adjuvant arthritis through osteoprotegerin ligand", *Nature,* 402:304–309 (1999).

Lange–Gustafson et al., "Purification and Properties of Int–h, a Variant Protein Involved in Site–specific Recombination of Bacteriophage λ", *J. Biol. Chem.,* 259(20):12724–12732 (1984).

Larin et al., "A method for linking yeast artificial chromosomes", *Nucl. Acid Res.,* 24(21):4192–4196 (1996).

Libert et al., "Construction of a Bovine Genomic Library of Large Yeast Artificial Chromosome Clones", *Genomics,* 18:270–276 (1993).

Lorbach et al., "Site–specific Recombination in Human Cells Catalyzed by Phage λ Integrase Mutants", *J. Mol. Biol.,* 296:1175–1181 (2000).

Lowry, R., "Two–Factor ANOVA with Repeated Measures on One Factor", http://faculty.vassar.edu/lowry/anova2corr.html (2000).

Luo et al., "Synthetic DNA delivery systems", *Nature Biotechnol.,* 18:33–37 (2000).

Marschall et al., "Transfer of YACs up to 2.3 Mb intact into human cells with polyethylenimine", *Gene Therapy,* 6:1634–1637 (1999).

Miller et al., "int–h: an int Mutation of Phage λ That Enhances Site–Specific Recombination", *Cell,* 20:721–729 (1980).

Mountain et al., "Gene therapy: the first decade", *TIBTECH,* 18:119–128 (2000).

NCBI Nucleotide, Gene Bank Accession No. NC001416.

Osborne et al., "Gene therapy for long–term expression of erythropoietin in rats", *Proc. Natl. Acad. Sci. USA,* 92:8055–8058 (1995).

Palmieri et al., "Construction of a pilot human YAC library in a recombination–defective yeast strain", *Gene,* 188:169–174 (1997).

Schedl et al., "A method for the generation of YAC transgenic mice by pronuclear microinjection", *Nucl. Acid Res.,* 21:4783–4787 (1993).

Shen et al., "A structurally defined mini–chromosome vector for the mouse germ line", *Current Biology,* 10:31–34 (2000).

Sigma Catalog, Biochemicals and Regents for Life Science Research, Molecular Biology, pp. 221, 227, 275, 363, 411, 543, 576, 909 (1998).

Stocum et al., "Regenerative biology: A millenial revolution", *Cell and Devel. Biol.,* 10:433–440 (1999).

Stocum et al., "Regenerative biology and engineering: strategies for tissue restoration", *Wound Rep. Reg.,* 6:276–290 (1998).

Takeda et al., "Construction of a bovine yeast artificial chromosome (YAC) library", *Animal Genetics,* 29:216–219 (1998).

Tao et al., "Cloning and stable maintenance of DNA fragments over 300 kb in *Escherichia coli* with conventional plasmid–based vectors", *Nucl. Acids Res.,* 26(21):4901–4909 (1998).

Toye et al., "A yeast artificial chromosome (YAC) library containing 10 haploid chicken genome equivalents", *Mammalian Genome,* 8:274–276 (1997).

Tsonis et al., "Regeneration in Vertebrates", *Devel. Biol.,* 221:273–284 (2000).

Uherek et al., "DNA–carrier proteins for targeted gene delivery", *Adv. Drug Delivery Reviews,* 44:153–166 (2000).

Urlaub et al., "Effect of Gamma Rays at the Dihydrofolate Reductase Locus: Deletions and Inversions", *Somatic Cell and Mol. Genetics,* 12(6):555–566 (1986).

Wada et al., "Chimeric YACs were generated at unreduced rates in conditions that suppress coligation", *Nucl. Acids Res.,* 2(9):1651–1654 (1994).

Zhong et al., "Zebrafish Genomic Library in Yeast Artificial Chromosomes", *Genomics,* 48:136–138 (1998).

Ohse, et al., "A New and Efficient Method for Gene Transfer into Mouse FM3A Cells Using Metaphase Chromosomes by Electroporation," *Biosci. Biotech Biochem.,* 60(11):1879–1811 (1996).

Wada, et al., "HPRT Yeast Artificial Chromosome Transfer into Human Cells By Four Methods and an Involvement of Homologous Recombination," *Biochemical and Biophysical Research Communications,* 200(3):1693–1700 (1994).

Batel, et al., "A Microplate Assay for DNA Damage Determination (*Fast Micromethod*)[1] in Cell Suspensions and Solid Tissues," *Anal Biochem.,* 270(2):195–200 (1999).

Bordignon, et al., "Gene Therapy in Peripheral Blood Lymphocytes and Bone Marrow for ADA Immunodeficient Patients," *Science,* 270:470–475 (1995).

Compton, et al., "An improved method for routine preparation of intact artificial chromosome DNA (340–1000 kb) for transfection into human cells," *Nucleic Acids Research* 27 (7):1762–1765 (1999).

David D. Dean, "Import of Plasmid DNA into the Nucleus Is Sequence Specific," *Experimental Cell Research,* 230:293–302 (1997).

Dowty, et al., "Plasmid DNA entry into postmitotic nuclei of primary rat myotubes", *Proc. Natl. Acad. Sci. USA,* 92:4572–4576 (1995).

Leahy, et al., "Novel Biotinylated Plasmid Expression Vectors Retain Biological Function and Can Bind Streptavidin," *Bioconjug Chem.,* 7:545–551 (1996).

Loyter, et al., "Mechanisms of DNA uptake by mammalian cells: Fate of exogenously added DNA monitored by the use of fluorescent dyes," *Proc. Natl. Acad. Sci. USA,* 79:422–426 (1982).

Mascarenhas, et al., "Gene Delivery to Human B–Precursor Acute Lymphoblastic Leukemia Cells," *Blood,* 92 (10):3537–3545 (1998).

Neves, et al., "Coupling of a targeting peptied to plasmid DNA by covalent triple helix formation," *FEBS Letter,t* 453(1–2):41–45 (1999).

Oberle, et al., "Efficient transfer of chromosome–based DNA constructs into mammalian cells," *Biochimica et Biophysica Acta 1676,* 223–230 (2004).

Tsuchiya, et al., "Characterization of a DNA Uptake Reaction through the Nuclear Membrane of Isolated Yeast Nuclei," *Journal of Bacteriology,* 170(2):547–551 (1988).

Zabner, et al., "Cellular and Molecular Barriers to Gene Transfer by a Cationic Lipid," *J. Biol. Chem,* 270(32):18997–19007 (1995).

Eck et al., "Goodman & Gilman's The Pharmacological Basis of Therapeutics", 9th Edition, Chapter 5, McGraw–Hill, NY.

Emanueli et al., "Angiogenesis gene therapy to rescue ischaemic tissues: achievements and future directions", *Br. J. Pharmacol.,* 133(7):951–958 (2001).

Marshall E., "Gene Therapy's Growing Pains", *Science,* 269(5227):10501055 (1995).

Orkin et al., "Report and Recommendations of the Panel To Assess the NIH Investment in Research on Gene Therapy", on line at http://www.nih.gov/news/panelrep.

Rissanen et al., "Gene therapy for therapeutic angiogenesis in critically ischaemic lower limb—on the way to the clinic", *Eur. J. Clin. Invest.,* 31(8):651–666 (2001).

Ross et al., "Gene Therapy in the United States: A Five–Year Status Report", *Hum. Gene. Ther.,* 7(14):1781–1790 (1996).

Rubanyi, G.M., "The future of human gene therapy", *Mol. Aspects Med.,* 22(3):113–142 (2001).

Schwaab et al., "Gene Therapy of Hemophilia", *Semin. Thromb. Hemost.,* 27(4):417–424 (2001).

Strauss et al., "Molecular complementation of a collagen mutation in mammalian cells using yeast artificial chromosomes", *EMBO J.,* 11(2):417–422 (1992).

Verma et al., "Gene therapy—promises, problems and prospects", *Nature,* 389(6648):239–242 (1997).

1999 Press Releases: "Chromos Molecular Systems Reports In Vitro and In Vivo Stability of Functional Mammalian Artificial Chromosome"; http://www.chromos.com/march1899.htm1.

1999 Press Releases: "Chromos Molecular Systems Demonstrates Large–Scale Isolation of Mammalian Artificial Chromosomes"; http://www.chromos.com/feb399.htm1.

2001 Press Releases: "Chromos Announces Publication of Rapid Screening Technique in the Journal Cytometry"; http://www.chromos.com/June%207.htm1.

2001 Press Releases: "Chromos Presents New Chromosome–Based Platform Technology for Gene Therapy (ASGT)"; http://www.chromos.com/Jun%204.htm1.

2001 Press Releases: "Chromos Initates Research into Plant Artificia Chromosomes"; http://www.chromos.com/Jan.23.htm1.

2001 Press Releases: "Chromos Announces Expression of Therapeutic Protein in Transgenic Animal Carrying an Artificial Chromosome"; http://www.chromos.com/nov8.htm1.

2001 Press Releases: "Chromos and Biological Research Center Announces Publication of Human Artificial Chromosome Methodology in the Journal of Cell Sciences"; http://www.chromos.com/sept12.htm1.

2001 Press Releases: "Chromos Reports Data on Transgenic Animals Carrying Artificial Chromosome"; http://www.chromos.com/march28.htm1.

Alton et al., "Nucleotide sequence analysis of the chloramphenicol resistance transposon Tn9", *Nature,* 282:864–869 (1979).

Anderson et al., "Flow Cytometry of Mitotic Cells", *Experimental Cell Res.,* 238:498–502 (1998).

Auduoy et al., "Serum as a modulator of lipoplex–mediated gene transfection: dependence of amphiphile, cell type and complex stability", *J. Gene Med.,* 2:465–476 (2000).

Baldwin et al., "Cloning of the Luciferase Structural Genes from *Vibrio harveyi* and Expression pf Bioluminescence in *Escherichia coli*", *Biochem.,* 23:3663–3667 (1984).

Bao et al., "Transfection Of A Reporter Plasmid Into Cultured Cells By Sonoporation in Vitro", *Ultrasound in Med. & Biol.,* 23/6:953–959 (1997).

Basic Protocol, Book: *Current Protocols in Molecular Biology,* Supplement 14, "Calcium Phosphate Transfection", Section 1, Unit 9.1.1–9.1.9.

Co et al., "Generation of transgenic mice and germline transmission of a mammalian artificial chromosome introduced into embryos by pronuclear microinjection", *Chromosome Res.,* 8:183–191 (2000).

Csonka et al., "Novel generation of human satellite DNA–based artificial chromosomes in mammalian cells", *J. of Cell Sci.*, 113:3207–3216 (2000).

de Jonge et al., "Chromosome and DNA–Mediated Gene Transfer in Cultured Mammalian Cells", *International Review of Cytology*, 92:133–158 (1984).

de Jong et al., Abstract No. 550: "In Vitro Transfer of a 60 Mb Mammalian Artificial Chromosome into Primary Cell Lines Using Cationic Lipids an a Dendrimer", one page.

de Jong et al., "Mammalian Artificial Chromosome Pilot Production Facility: Large–Scale Isolation of Functional Satellite DNA–Based Artificial Chromosomes", *Cytometry*, 35:129=133 (1999).

de Wet et al., "Firefly Luciferase Gene: Structure and Expression in Mammalian Cells", *Molecular and Cellular Biol.*, 7/2:725–737 (1987).

Durand et al., "Response of Cell Subpopulations in Spheroids to Radiation–Drug Combinations", *NCI Monogr.*, 6:95–100 (1988).

Durand et al., "Schedule Dependence for Cisplatin and Etoposide Multifraction Treatments of Spheroids", *J. Natl. Cancer Inst.*, 82/23:1841–1845 (1990).

Durand et al., "Sequencing Radiation and Adriamycin Exposures in Spheroids to Maximize Therapeutic Gain", *I. J. Radiation Oncol. Biol. Phys.*, 17/2:345–350 (1989).

Engebrecht et al., "Identification of genes and gene products necessary for bacterial bioluminescence", *Proc. Natl. Acad. Sci. USA*, 81:4154–4158 (1984).

Fritz et al., Abstract: "Ultrasound Enhancement of Gene Expression, Newly Discovered Cationic Lipids, and a New Class of Gene Delivery Agents", ImaRx Pharmaceutical Corp. Announces Important Discoveries in Emerging Field of Drug Delivery Using Acoustically Active Carriers, ImaRx Pharmaceutical Corp., pp. 1–2 (2001).

Graham et al., "A New Technique for the Assay of Infectivity of Human Adenovirus 5 DNA", *Virol.*, 52:456–467 (1973).

Gratzner et al., "An Immunofluorescence Method for Monitoring DNA Synthesis by Flow Cytometry", *Cytometry*, 1/6:385–389 (1981).

Haas et al., "Codon usage limitation in the expression of HIV–1 envelope glycoprotein", *Current Biol.*, 6/3:315–324 (1996).

Hall et al., "Expression and Regulation of *Escherichia coli* lacZ Gene Fusions in Mammalian Cells", *J. Molecular and Applied Genetics*, 2:101–109 (1983).

Hoekstra et al., "Lipid trafficking and sorting: how cholesterol is filling gaps", *Current Opinion in Cell Biol.*, 12:496–502 (2000).

Hoekstra et al., "Membrane flow, lipid sorting and cell polarity in HepG2 cells, role of a subapical compartment", *Biochem. Soc. Trans.*, 27/4:422–428 (1999).

Hoffman et al., "Lipochromosome Mediated Gene Transfer: Identification And Probable Specificity Of Localization Of Human chromosomal Material And Stability Of The Transferents", *In Vitro*, 17/8:735–740 (1981).

Hollo et al., "Evidence for a megareplicon covering megabases of centromeric chromosome segments", *Chromo. Res.*, 4:240–247 (1996).

Huang et al., "Intervening sequences increase efficiency of RNA 3' processing and accumulation of cytoplasmic RNA", *Nucleic Acids Res.*, 18/4:937–947 (1990).

Huber et al., "A Comparison Of Shock Wave And Sinusoidal–Focused Ultrasound=Induced Localized Transfection Of HeLa Cells", *Ultrasound to Med. & Biol.*, 25/9:1451–1457 (1999).

Ishihara et al., "Effects of phospholipid adsorption on non-thrombogenicity of polymer with phospholipid polar group", *J. Biomed. Materials Res.*, 27:1309–1314 (1993).

Jackson et al., "The novel mechanism of initiation of picornavirus RNA translation", *TIBS*, 15:477–483 (1990).

Jang et al., "A Segment of the 5' Nontranslated Region of Encephalomyocarditis Virus RNA Directs Internal Entry of Ribosomes during In Vitro Translation", *J. Virol.*, 62/8:2636–2643 (1988).

Jellinek et al., "Potent 2'–Amino–2'–deoxypyrimidine RNA Inhibitors of Basic Fibroblast Growth Factor", *Biochem.*, 34:11363–11372 (1995).

Kereso et al., "De novo chromosome formations by large–scale amplification of the centromeric region of mouse chromosomes", *Chromosome Res.*, 4:226–239 (1996).

Kim et al., "Ultrasound–Mediated Transfection of Mammalian Cells", *Human Gene Therapy*, 7:1339–1346 (1996).

Lamb et al., "Introduction and expression on the 400 kilobase precursor amyloid protein gene in transgenic mice", *Nature Genetics*, 5:22–29 (1993).

Lin et al., "Modified RNA sequence pools for in vitro selection", *Nucleic Acids Res.*, 22/24:5229–5234 (1994).

Maier et al., "Membrane domains and polarized trafficking of sphingolipids", *Cell & Develop. Biol.*, 12:149–161 (2001).

Miller et al., "Sonoporation Of Cultured Cells In The Rotating Tube Exposure System", *Ultrasound in Med. & Biol.*, 25/1:143–149 (1999).

Mukherjee et al., "Entrapment of metaphase chromosomes into phospholipid vesicles (lipochromosomes): Carrier potential in gene transfer", *Proc. Natl. Acad. Sci. USA*, 75/3:1361–1365 (1978).

Noguchi et al., "Measurement of DNA Synthesis by Flow Cytometry", *Cytometry*, 1/6:390–393 (1981).

Oberle et al., "Lipoplex Formation under equilibrium Conditions Reveals a Three–Step Mechanism", *Biophys. J.*, 79:1447–1454 (2000).

Olive et al., "Increase in the fraction of necrotic, not apoptotic, cells in SiHa xenograft tumours shortly after irradiation", *Radiotherapy & Oncology*, 50:113–119 (1999).

Olive et al., "Resistance to DNA Denaturation in Irradiated Chinese Hamster V79 Fibroblasts Is Linked to Cell Shape", *Experimental Cell Res.*, 193:339–345 (1991).

Pagratis et al., "Potent 2'–amino–, and 2'–fluoro–2'–deoxyribonucleotide RNA inhibitors of keratinocyte growth factor", *Nature Biotechnol.*, 15:68–73 (1997).

Pecheur et al., "Protein–induced Fusion Can Be Modulated by Target Membrane Lipids through a Structural Switch at the Level of the Fusion Peptide", *J. Biol. Chem.*, 275/6:3936–3942 (2000).

Perez et al., "Satellite DNA–based artificial chromosomes—chromosomal vectors", *TIBTECH*, 18:402–403 (2000).

Pittman et al., "A simple and rapid immunological technique for visualising chromosome–mediated gene transfer (CMGT)", *J. Immunol. Methods*, 103:87–92 (1987).

Ropp et al., "Aequorea Green Fluorescent Protein Analysis by Flow Cytometry", *Cytometry*, 21:309–317 (1995).

Sambrook et al., Book: "Molecular Cloning", *A Laboratory Manual*, Second Ed., Cold Spring Harbor Laboratory Press (1989) Table of Contents.

Shi et al., "Efficient cationic lipid–mediated delivery of antisense oligonucleotides into eukaryotic cells: down–regulation of the corticotropin–releasing factor receptor", *Nucleic Acids Res.*, 29/10:2079–2087 (2001).

Song et al., "Cell surface expression of MHC molecules in glioma cells infected with herpes simplex virus type–1", *J. NeuroImmunol.*, 93:1–7 (1999).

Takeuchi et al., "Enhanced Visualization of Intravascular and Left Atrial Appendage Thrombus with the Use of Thrombus–Targeting Ultrasonographic Contrast Agent (MRX–408A1): In Vivo Experimental Echocardiographic Studies", *J. Am. Soc. Echocardiogr.*, 12/12:1015–1021 (1999).

Telenius et al., "Stability of a functional murine satellite DNA–based artificial chromosome across mammalian species", *Chromosome Res.*, 7:3–7 (1999).

Toh et al., "Isolation and characterization of a rat liver alkaline phosphatase gene. A single gene with two promoters", *FEBS*, pp. 231–237 (1989).

Unger et al., Abstract: "Assessment of Myocardial Infarct with a New Ultrasound Contrast Agent", *RSNA*, Chicago, Il #1177, p. 419 (1997).

Unger et al., Abstract: "Ultrasound–Mediated Drug Delivery with Acoustically Active Carriers and SonoPorationTM and FluoroGeneTM Gene Delivery", *ImaRx Pharmaceutical Corp.*, pp. 1–8 (2000).

Unger et al., Book: 16th International Congress on Acoustics and 135th Meeting Acoustical Society of America, "Gas–Filled Liposomes as Ultrasound Contrast Agents for Blood Pool, Thrombus–Specific and Therapeutic Applications", 3:2179–2180 (1998).

Unger et al., Book: "Liposomes as myocardial perfusion ultrasound contrast agents", *Ultrasound contrast Agents*, Chapter 6, pp. 57–74 (1997).

Unger et al., "Ultrasound Enhances Gene Expression of Liposomal Transfection", *Invest. Radiol.*, 32:723–727 (1997).

Vanderbyl et al., "A Flow Cytometry Technique for Measuring Chromosome–Mediated Gene Transfer", *Cytometry*, 44:100–105 (2001).

van der Woude et al., "Novel pyridinium surfactants for efficient, nontoxic in vitro gene delivery", *Proc. Natl. Acad. Sci. USA*, 94:1160–1165 (1997).

van der Woude et al., "Parameters influencing the introduction of plasmid DNA into cells by the use of synthetic amphiphiles as a carrier system", *BBA Biochimica et Biophysica Acta*, 1240:34–40 (1995).

van Leeuwen et al., "Transfection of Small Numbers of Human Endothelial Cells by Electroporation and Synthetic Amphiphiles", *Eur. J. Vase Endovasc. Surg.*, 17:9–14 1999).

Wigler et al., "DNA–mediated transfer of the adenine phosphoribosyltransferase locus into mammalian cells", *Proc. Natl. Acad. Sci. USA*, 76/3:1373–1376 (1979).

Wong et al., "Sequence organization and cytological localization of the minor satellite of mouse", *Nucleic Acids Res.*, 16:11645–11661 (1988).

Wyber et al., "The Use of Sonication of r the Efficient Delivery of Plasmid DNA into Cells", *Pharmaceutical Res.*, 14/6:750–756 (1997).

Yang et al., "Optimized codon usage and chromophore mutations provide enhanced sensitivity with the green fluorescent protein", *Nucleic Acids Res.*, 24/22:4592–4593 (1996).

Caldwell et al. "Activation of Genes with Ultrasound," *Ultrasound Contrast Research Symposium* San Diego, CA Feb. 6–8, 1998.

\* cited by examiner

METHODS FOR DELIVERING NUCLEIC ACID MOLECULES INTO CELLS AND ASSESSMENT THEREOF

RELATED APPLICATIONS

This application is related to the U.S. application Ser. No. 09/815,979, to de Jong et al., entitled "METHODS FOR DELIVERING NUCLEIC ACID MOLECULES INTO CELLS AND ASSESSMENT THEREOF." The subject matter thereof is incorporated in its entirety by reference thereto.

FIELD OF THE INVENTION

The present invention relates to methods of delivering nucleic acid molecules into cells and methods for measuring nucleic acid delivery into cells and the expression of the nucleic acids therein.

BACKGROUND OF THE INVENTION

A number of methods of delivering nucleic acid molecules, particularly plasmid DNA and other small fragments of nucleic acid, into cells have been developed. These methods are not ideal for delivery of larger nucleic acid molecules. Thus, there is a need for methods of delivering nucleic acid molecules of increasing size and complexity, such as artificial chromosomes, into cells. Methods are required for use with in vitro and in vivo procedures such as gene therapy and for production of transgenic animals and plants. Furthermore, there is a need for the ability to rapidly and simply determine and assess the efficiency of delivery of DNA into cells.

Therefore it is an object herein to provide methods for delivering nucleic acid molecules, particularly larger molecules, including artificial chromosomes, into cells. Methods for assessing delivery are also provided.

SUMMARY OF THE INVENTION

Methods for delivery of large nucleic acid molecules into cells are provided. The methods, which can be used to deliver nucleic acid molecules of any size, are suitable for delivery of larger nucleic acid molecules, such as natural and artificial chromosomes and fragments thereof, into cells. The methods are designed for in vitro, ex vivo and in vivo delivery of nucleic acid molecules for applications, including, but limited to, delivery of nucleic acid molecules to cells for cell-based protein production, transgenic protein production and gene therapy. Methods of protein production in cells and in transgenic animals and plants, methods of introducing nucleic acid into cells to produce transgenic animals and plants, and methods for ex vivo and in vivo gene therapy are also provided.

Methods provided herein are designed for delivering a large nucleic acid molecule into a cell, but may also be used to deliver smaller molecules. The methods include the steps of exposing the nucleic acid molecule to a first delivery agent, typically an agent that increases contact between the nucleic acid molecule and the cell; and exposing the cell to a second delivery agent, which is generally different from the first agent, and is particularly an agent, such as energy, that enhances permeability of the cell. Selected delivery agents and combinations thereof are those that result in delivery of the nucleic acid the cell to a greater extent than in absence of the agent or in the presence of one of the agent alone. In all of these methods, if the permeability enhancing agent is energy, such as electroporation or sonoporation, the cell is contacted therewith in the absence of the nucleic acid molecule.

Also provided are methods in which the cells are contacted with a lipid agent, particularly a dendrimer, such as SAINT-2™ (1-methyl-4-(1-octadec-9-enyl-nonadec-10-enylenyl) pyridinium chloride, also designated 1-methyl-4-(19-cis,cis-hepatritiaconta-9,28-dienyl) pyridinium chloride), simultaneously with or sequentially with application of energy. The nucleic acid, which is optionally, although preferably not treated with a delivery agent, is contacted with the so-treated cell.

The selected delivery methods vary depending on the target cells (cells into which nucleic acid is delivered), the nucleic acid molecules, and the type(s) of delivery agent(s) selected. Exemplary methods for delivery of large nucleic acid molecules into cells provided herein include, but are not limited to, methods involving any of the following:

mixing the nucleic acid molecule with a delivery agent, such as a cationic lipid that neutralizes the charge of the nucleic acid, and contacting the cell with the mixture of nucleic acid and delivery agent;

contacting a cell with the nucleic acid molecule, and then contacting the cell with a delivery agent or contacting a cell with a delivery agent then contacting the cell with the nucleic acid molecule;

contacting a cell in the absence of the nucleic acid molecule with a delivery agent, applying ultrasound or electrical energy to the cell contacted with the delivery agent, and contacting the cell with the nucleic acid molecule upon the conclusion of the application of the energy;

applying ultrasound or electrical energy to a cell, and contacting the cell, upon conclusion of the application of the energy, with a mixture of the nucleic acid molecule and a delivery agent;

applying ultrasound or electrical energy to a cell, contacting the cell with a delivery agent upon conclusion of the application of the energy and contacting the cell previously contacted with the delivery agent with the nucleic acid molecule;

applying ultrasound or electrical energy to a cell and contacting the cell with the nucleic acid molecule upon conclusion of the application of the energy;

contacting a cell in the absence of the nucleic acid molecule with a delivery agent, applying ultrasound or electrical energy to the cell contacted with the delivery agent, and contacting the cell with a mixture of the nucleic acid and a delivery agent upon the conclusion of the application of the energy.

Although combinations of the above methods may be used, it has been found that any application of energy to the cells must be done prior to introduction of the nucleic acid molecule.

The methods provided herein are intended for delivery of large nucleic acid molecules into cells in a variety of environments for a variety of purposes. For example, nucleic acid molecules greater than about 0.5, 0.6. 0.7, 0.8, 0.9, 1, 5, 10, 30, 50 and 100 megabase pairs may be delivered into cells using the methods provided herein. The methods may be used to deliver the large nucleic acid molecules into cells in vitro or in vivo.

In in vivo applications of the delivery methods, such as in in vivo gene therapy, large nucleic acid molecules may be delivered to cells directly in an animal subject, and in particular human subjects. Reagents can be administered locally or systemically (e.g., in the bloodstream) in the subject. For example, local administration of the nucleic acids, and/or delivery agents, may be into areas such as joints, the skin, tissues, tumors and organs. For systemic administration, the nucleic acid molecules may be targeted to cells or tissues of interest.

The delivery methods provided herein may also be used to deliver large nucleic acid molecules to a target cell in vitro which is then introduced into an animal subject, in particular human subjects, such as may be done, for example, in a method of ex vivo gene therapy. Thus, also provided herein are methods of in vivo and ex vivo gene therapy using the methods for delivering large nucleic acid molecules into cells as provided herein.

In particular embodiments of the methods in which a delivery agent is used, the delivery agent is a cationic compound. Cationic compounds include, but are not limited to, a cationic lipid, a cationic polymer, a mixture of cationic lipids, a mixture of cationic polymers, a mixture of a cationic lipid and a cationic polymer and a mixture of a cationic lipid and a neutral lipid, polycationic lipids, non-liposomal forming lipids, activated dendrimers, ethanolic cationic lipids, cationic amphiphiles and pyridinium chloride surfactants.

Included among the nucleic acid molecules that may be delivered into cells using the methods provided herein are artificial chromosomes, satellite DNA-based artificial chromosomes (SATACs, herein referred to as ACes) and natural chromosomes or fragments of any of these chromosomes.

The ultrasound energy can be applied as one continuous pulse or two or more intermittent pulses. The intermittent pulses of the ultrasound energy can be applied for substantially the same length of time, at substantially the same energy level or can vary in energy level, the length of time applied, or energy level and the length of time applied. Ultrasound energy ranges and number of pulses can vary, from methods provided herein, according to the instrument selected and can be empirically determined. Typically, ultrasound will be applied for about 30 seconds to about 5 minutes. The power used is a function of the sonorporator used.

The effects of the ultrasound energy may be enhanced by contacting a cell (in vitro) or administering to a subject (in vivo) a cavitation compound prior to the application of ultrasound energy. Thus, the provided methods may include the use of such cavitation compounds.

When electric fields are employed in the methods provided herein, they are preferably applied to the cells in suspension for about 20 to 50 msec, but the timing and voltage is a function of the instrument used and the particular parameters. The electrical energy can be applied as one to five intermittent pulses. As noted, electrical field ranges and number of pulses can vary according to instrument specification and can be determined empirically.

Methods are provided for generating transgenic animals, particularly non-human transgenic animals, by delivering large nucleic acid molecules into animal cells, in particular non-human animal cells, using delivery methods provided herein, and exposing the animal cells into which the large nucleic acid molecules are delivered to conditions whereby a transgenic animal develops therefrom.

The methods for delivering large nucleic acid molecules into cells provided herein may also be used in methods of generating transplantable organs and tissues. Exemplary cells for use in methods of generating transgenic animals, particularly non-human transgenic animals, or transplantable organs include, but are not limited to, an embryonic stem cell, a nuclear transfer donor cell, a stem cell and a cell that is capable of the generation of a specific organ. The methods for delivering nucleic acid molecules into cells provided herein may also be used in methods of generating cellular protein production cell lines.

Further provided are methods for monitoring delivery of nucleic acids into a cell. These methods permit the rapid and accurate measurement of nucleic acid transfer into cells, thus allowing for screening and optimizing the use of various delivery agents and protocols for delivery of any nucleic acid into any cell type, in vitro, ex vivo or in vivo. Further provided are methods to monitor delivery and expression of nucleic acids in a cell.

In embodiments of the methods for monitoring delivery of nucleic acids into a cell, labeled nucleic acid molecules, such as DNA, are delivered into the cell using the delivery agent(s) as described herein, or using any delivery method known to those of skill in the art. A detection method, such as flow cytometry, is then used to determine the number of cells containing the label as an indication of the ability of the delivery method to facilitate or effect delivery of the nucleic acid molecules. Other detection methods that may be used in place of or in addition to flow cytometry include, but are not limited to, fluorimetry, cell imaging, fluorescence spectroscopy and other such methods known to those of skill in the art for such detection and, as needed or desired, for quantitation.

In an exemplary embodiment of the methods for monitoring and quantifying delivery of nucleic acid molecules, such as DNA, into cells, the nucleic acid molecule is an artificial chromosome labeled with a nucleoside or ribonucleoside analog, particularly a thymidine analog, such as iododeoxyuridine (IdU or IdUrd) and bromodeoxyuridine (BrdU), and the delivery agent is a cationic compound, which is used alone or in combination with energy.

Because of the ease with which numbers of events are collected, the monitoring methods provided herein, particularly those based on flow cytometry techniques, provide a method for collection of nucleic acid molecule delivery data that is statistically superior to previous methods of evaluating nucleic acid molecules transfer. The positive values are instrument derived and therefore are not susceptible to judgement errors.

The monitoring methods provided herein permit the rapid, simple and accurate detection of delivery of small numbers of nucleic acid molecules into cells. Such small numbers may be sufficient for purposes of transgenesis, gene therapy, cellular protein production and other goals of gene transfer. The monitoring methods also make it possible to rapidly quantify differences in delivery efficiencies of differing delivery methods and thus facilitate the development and optimization of methods for the delivery of nucleic acid molecules, such as DNA, into cells.

These methods can also be used to optimize transfection efficiencies into cells for which no delivery protocol has been established or which are not easily transfected. These methods also permit rapid screening of delivery protocols and agents for their ability to enhance or permit delivery of nucleic acid molecules, such as DNA, of any size into a cell.

Methods are also provided that combine methods of monitoring nucleic acid molecule delivery with methods for monitoring expression of nucleic acid molecules. It is possible not only to assess the efficiency of delivery of nucleic acid molecules to cells, but also to monitor the subsequent expression of the delivered nucleic acid molecules in the same cell population. Thus, these methods also provide a method for the mapping of biological events between nucleic acid molecule delivery and early gene expression, using marker genes, such as, but are not limited to, fluorescent proteins, such as red, green or blue fluorescent proteins. In a particular embodiment of these combined methods, delivery and expression of nucleic acid molecules, such as delivery of a chromosome and expression of genes encoded thereon, are monitored by IdU labeling of a nucleic acid molecule that contains sequences encoding a green fluorescent protein.

In particular embodiments, the methods of monitoring delivery and expression of a nucleic acid molecule include the steps of: introducing labelled nucleic acid molecules that encode a reporter gene into cells; detecting labelled cells as an indication of delivery of the nucleic acid into a cell; and measuring the product of the reporter gene as an indication of DNA expression in the cell, whereby delivery and expression of nucleic acid molecules in the cell is detected or determined. The labelled cells can be detected, for example, by flow cytometry, fluorimetry, cell imaging or fluorescence spectroscopy. The label, for example, can be iododeoxyuridine (IdU or IdUrd) or bromodeoxyuridine (BrdU), the reporter gene, for example, can be one that encodes fluorescent protein, enzyme, such as a luciferase, or antibody. The delivered nucleic acid molecules include, but are not limited to, RNA, including ribozymes, DNA, including naked DNA and chromosomes, plasmids, chromosome fragments, typically containing at least one gene or at least 1 Kb, naked DNA, or natural chromosomes. The method is exemplified herein by determining delivery and expression of artificial chromosome expression systems (ACes). Any types of cells, eukaryotic and prokaryotic, including cell lines, primary cell lines, plant cells, and animal cells, including stem cells, embryonic cells, and other cells into which delivery of a nucleic acid molecule can occur is contemplated.

DETAILED DESCRIPTION OF THE INVENTION

A. Definitions

Unless defined otherwise, all technical and scientific terms used herein have the same meaning as is commonly understood by one of skill in the art to which this invention belongs. All patents, patent applications and publications referred to herein are incorporated by reference.

As used herein, "nucleic acid" refers to a polynucleotide containing at least two covalently linked nucleotide or nucleotide analog subunits. A nucleic acid can be a deoxyribonucleic acid (DNA), a ribonucleic acid (RNA), or an analog of DNA or RNA. Nucleotide analogs are commercially available and methods of preparing polynucleotides containing such nucleotide analogs are known (Lin et al. (1994) *Nucl. Acids Res.* 22:5220–5234; Jellinek et al. (1995) *Biochemistry* 34:11363–11372; Pagratis et al. (1997) *Nature Biotechnol.* 15:68–73). The nucleic acid can be single-stranded, double-stranded, or a mixture thereof. For purposes herein, unless specified otherwise, the nucleic acid is double-stranded, or it is apparent from the context.

The term "nucleic acid" refers to single-stranded and/or double-stranded polynucleotides, such as deoxyribonucleic acid (DNA) and ribonucleic acid (RNA), as well as analogs or derivatives of either RNA or DNA. Also included in the term "nucleic acid" are analogs of nucleic acids such as peptide nucleic acid (PNA), phosphorothioate DNA, and other such analogs and derivatives.

As used herein, DNA is meant to include all types and sizes of DNA molecules including cDNA, plasmids and DNA including modified nucleotides and nucleotide analogs.

As used herein, nucleotides include nucleoside mono-, di-, and triphosphates. Nucleotides also include modified nucleotides, such as, but are not limited to, phosphorothioate nucleotides and deazapurine nucleotides and other nucleotide analogs.

As used herein, the term "large nucleic acid molecules" or "large nucleic acids" refers to a nucleic acid molecule of at least about 0.5 megabase pairs (Mbase) in size, greater than 0.5 Mbase, including nucleic acid molecules at least about 0.6. 0.7, 0.8, 0.9, 1, 5, 10, 30, 50 and 100, 200, 300, 500 Mbase in size. Large nucleic acid molecules typically may be on the order of about 10 to about 450 or more Mbase, and may be of various sizes, such as, for example, from about 250 to about 400 Mbase, about 150 to about 200 Mbase, about 90 to about 120 Mbase, about 60 to about 100 Mbase and about 15 to 50 Mbase.

Examples of large nucleic acid molecules include, but are not limited to, natural chromosomes and fragments thereof, especially mammalian chromosomes and fragments thereof which retain a centromere and telomeres, artificial chromosome expression systems (ACEs; also called satellite DNA-based artificial chromosomes (SATACs); see U.S. Pat. Nos. 6,025,155 and 6,077,697), mammalian artificial chromosomes (MACs), plant artificial chromosomes, insect artificial chromosomes, avian artificial chromosomes and minichromosomes (see, e.g., U.S. Pat. Nos. 5,712,134, 5,891, 691 and 5,288,625). The large nucleic acid molecules may include a single copy of a desired nucleic acid fragment encoding a particular nucleotide sequence, such as a gene of interest, or may carry multiple copies thereof or multiple genes or different heterologous sequences of nucleotides. For example, ACes can carry 40 or even more copies of a gene of interest. Large nucleic acid molecules may be associated with proteins, for example chromosomal proteins, that typically function to regulate gene expression and/or participate in determining overall structure.

As used herein, an artificial chromosome is a nucleic acid molecule that can stably replicate and segregate alongside endogenous chromosomes in a cell. It has the capacity to act as a gene delivery vehicle by accommodating and expressing foreign genes contained therein. A mammalian artificial chromosome (MAC) refers to chromosomes that have an active mammalian centromere(s). Plant artificial chromosomes, insect artificial chromosomes and avian artificial chromosomes refer to chromosomes that include plant, insect and avian centromeres, respectively. A human artificial chromosome (HAC) refers to chromosomes that include human centromeres. For exemplary artificial chromosomes, see, e.g., U.S. Pat. Nos. 6,025,155; 6,077,697; 5,288,625; 5,712,134; 5,695,967; 5,869,294; 5,891,691 and 5,721,118 and published International PCT application Nos, WO 97/40183 and WO 98/08964.

As used herein, the term "satellite DNA-based artificial chromosome (SATAC)" is interchangable with the term "artificial chromosome expression system (ACes)". These artificial chromosomes are substantially all neutral non-coding sequences (heterochromatin) except for foreign heterologous, typically gene-encoding nucleic acid, that is interspersed within the heterochromatin for the expression therein (see U.S. Pat. Nos. 6,025,155 and 6,077,697 and International PCT application No. WO 97/40183). Foreign genes contained in these artificial chromosome expression systems can include, but are not limited to, nucleic acid that encodes traceable marker proteins (reporter genes), such as fluorescent proteins, such as green, blue or red fluorescent proteins (GFP, BFP and RFP, respectively), other reporter genes, such as β-galactosidase and proteins that confer drug resistance, such as a gene encoding hygromycin-resistance. Other examples of heterologous DNA include, but are not limited to, DNA that encodes therapeutically effective substances, such as anti-cancer agents, enzymes and hormones, and DNA that encodes other types of proteins, such as antibodies.

As used herein, the terms "heterologous" and "foreign" with reference to nucleic acids, such as DNA and RNA, are used interchangeably and refer to nucleic acid that does not occur naturally as part of a genome or cell in which it is present or which is found in a location(s) and/or in amounts in a genome or cell that differ from the location(s) and/or amounts in which it occurs in nature. It is nucleic acid that is not endogenous to the cell and has been exogenously introduced into the cell. Examples of heterologous DNA include, but are not limited to, DNA that encodes a gene product or gene product(s) of interest introduced into cells, for example, for purposes of gene therapy, production of transgenic animals or for production of an encoded protein. Other examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies.

As used herein, "delivery," which is used interchangeably with "transfection," refers to the process by which exogenous nucleic acid molecules are transferred into a cell such that they are located inside the cell. Delivery of nucleic acids is a distinct process from expression of nucleic acids.

As used herein, "expression" refers to the process by which nucleic acid is translated into peptides or is transcribed into mRNA and translated into peptides, polypeptides or proteins. If the nucleic acid is derived from genomic DNA, expression may, if an appropriate eukaryotic host cell or organism is selected, include splicing of the mRNA. For heterologous nucleic acid to be expressed in a host cell, it must initially be delivered into the cell and then, once in the cell, ultimately reside in the nucleus.

As used herein, cell recovery refers to a "total cell yield" after a specified time frame, which for purposes herein is twenty-four hours, and when used with reference to calculation of the clonal fraction As used herein, cell recovery time refers to a time frame in order for a cell to equilibrate to new conditions.

As used herein, cell survival refers to cell viability after a cytotoxic event, such as a delivery procedure.

As used herein, control plating efficiency (CPE) refers to the fraction of untreated cells, under standard optimal growth conditions for the particular cells, that survive a plating procedure. Plating efficiency refers to the fraction of treated cells that survive a plating procedure.

As used herein, clonal fraction is a measurement of cell recovery after delivery of exogenous nucleic acids into cells and the plating efficiency of the cells.

As used herein, transfer efficiency is the percentage of the total number of cells to which nucleic acids are delivered that contain delivered nucleic acid.

As used herein, transfection efficiency is the percentage of the total number of cells to which nucleic acids including a selectable marker are delivered that survive selection.

As used herein, index of potential transfection efficiency means the theoretical maximum transfection efficiency for a particular cell type under particular conditions, for example particular concentrations or amounts of particular delivery agents.

As used herein, the term "cell" is meant to include cells of all types, of eukaryotes and prokaryotes, including animals and plants.

As used herein, "delivery agent" refers to compositions, conditions or physical treatments to which cells and/or nucleic acids may be exposed in the process of transferring nucleic acids to cells in order to facilitate nucleic acid delivery into cells. Delivery agents include compositions, conditions and physical treatments that enhance contact of nucleic acids with cells and/or increase the permeability of cells to nucleic acids. In all instances, nucleic acids are not directly treated with energy, such as sonoporation.

As used herein, cationic compounds are compounds that have polar groups that are positively charged at or around physiological pH. These compounds facilitate delivery of nucleic acid molecules into cells; it is thought this is achieved by virtue of their ability to neutralize the electrical charge of nucleic acids. Exemplary cationic compounds include, but are not limited to, cationic lipids or cationic polymers or mixtures thereof, with or without neutral lipids, polycationic lipids, non-liposomal forming lipids, ethanolic cationic lipids and cationic amphiphiles. Contemplated cationic compounds also include activated dendrimers, which are spherical cationic polyamidoamine polymers with a defined spherical architecture of charged amino groups which branch from a central core and which can interact with the negatively charged phosphate groups of nucleic acids (e.g., starburst dendrimers).

Cationic compounds for use as delivery agents also include mixtures of cationic compounds that include peptides and protein fragments. The additional components may be non-covalently or covalently bound to the cationic compound or otherwise associated with the cationic compound.

As used herein, ultrasound energy is meant to include sound waves (for external application) and lithotripter-generated shock waves (for internal application).

As used herein, electrical energy is meant to include the application of electric fields to cells so as to open pores in membranes for the delivery of molecules into the cell, e.g., electroporation techniques.

As used herein, cavitation compound is meant to include contrast agents that are typically used with ultrasound imaging devices and includes gas encapsulated and nongaseous agents. These cavitation compounds enhance the efficiency of energy delivery of acoustic or shock waves.

As used herein, "pharmaceutically acceptable" as used herein refers to compounds, compositions and dosage forms that are suitable for administration to the subject without causing excessive toxicity, irritation, allergic response or other undesirable complication.

As used herein, embryonic stem cells are primitive, immature cells that are precursors to stem cells.

As used herein, stem cells are primitive, immature cells that are precursors to mature, tissue specific cells.

As used herein, nuclear transfer donor cells are cells that are the source of nuclei, which are transferred to enucleated oocytes during the process of nuclear transfer.

As used herein, the term "subject" refers to animals, plants, insects, and birds into which the large DNA molecules may be introduced. Included are higher organisms, such as mammals and birds, including humans, primates, cattle, pigs, rabbits, goats, sheep, mice, rats, guinea pigs, cats, dogs, horses, chicken and others.

As used herein, "administering to a subject" is a procedure by which one or more delivery agents and/or large nucleic acid molecules, together or separately, are introduced into or applied onto a subject such that target cells which are present in the subject are eventually contacted with the agent and/or the large nucleic acid molecules.

As used herein, "applying to a subject" is a procedure by which target cells present in the subject are eventually contacted with energy such as ultrasound or electrical energy. Application is by any process by which energy may be applied.

As used herein, gene therapy involves the transfer or insertion of nucleic acid molecules, and, in particular, large nucleic acid molecules, into certain cells, which are also referred to as target cells, to produce specific gene products that are involved in correcting or modulating diseases or disorders. The nucleic acid is introduced into the selected target cells in a manner such that the nucleic acid is expressed and a product encoded thereby is produced. Alternatively, the nucleic acid may in some manner mediate expression of DNA that encodes a therapeutic product. This product may be a therapeutic compound, which is produced in therapeutically effective amounts or at a therapeutically useful time. It may also encode a product, such as a peptide or RNA, that in some manner mediates, directly or indirectly, expression of a therapeutic product. Expression of the nucleic acid by the target cells within an organism afflicted with a disease or disorder thereby provides a way to modulate the disease or disorder. The nucleic acid encoding the therapeutic product may be modified prior to introduction into the cells of the afflicted host in order to enhance or otherwise alter the product or expression thereof.

For use in gene therapy, cells can be transfected in vitro, followed by introduction of the transfected cells into the body of a subject. This is often referred to as ex vivo gene therapy. Alternatively, the cells can be transfected directly in vivo within the body of a subject.

As used herein, flow cytometry refers to processes that use a laser based instrument capable of analyzing and sorting out cells and or chromosomes based on size and fluorescence.

As used herein, a reporter gene includes any gene that expresses a detectable gene product, which may be RNA or protein. Preferred reporter genes are those that are readily detectable. Examples of reporter genes include, but are not limited to nucleic acid encoding a fluoescent protein, CAT (chloramphenicol acetyl transferase) (Alton and Vapnek (1979), *Nature* 282: 864–869) luciferase, and other enzyme detection systems, such as beta-galactosidase; firefly luciferase (deWet et al. (1987), *Mol. Cell. Biol.* 7: 725–737); bacterial luciferase (Engebrecht and Silverman (1984), *PNAS* 1: 4154–4158; Baldwin et al. (1984), *Biochemistry* 23: 3663–3667); and alkaline phosphatase (Toh et al. (1989) *Eur. J. Biochem.* 182: 231–238, Hall et al. (1983) *J. Mol. Appl. Gen.* 2: 101).

As used herein, a reporter gene construct is a DNA molecule that includes a reporter gene operatively linked to a transcriptional control sequence. The transcriptional control sequences include the promoter and other optional regulatory regions, such as enhancer sequences, that modulate the activity of the promoter, or control sequences that modulate the activity or efficiency of the RNA polymerase that recognizes the promoter, or control sequences that are recognized by effector molecules, including those that are specifically induced by interaction of an extracellular signal with a cell surface protein. For example, modulation of the activity of the promoter may be effected by altering the RNA polymerase binding to the promoter region, or, alternatively, by interfering with initiation of transcription or elongation of the mRNA. Such sequences are herein collectively referred to as transcriptional control elements or sequences. In addition, the construct may include sequences of nucleotides that alter translation of the resulting mRNA, thereby altering the amount of reporter gene product.

As used herein, promoter refers to the region of DNA that is upstream with respect to the direction of transcription of the transcription initiation site. It includes the RNA polymerase binding and transcription imitation sites and any other regions, including, but not limited to repressor or activator protein binding sites, calcium or cAMP responsive sites, and any such sequences of nucleotides known to those of skill in the art to alter the amount of transcription from the promoter, either directly or indirectly.

As used herein, a promoter that is regulated or mediated by the activity of a cell surface protein is a promoter whose activity changes when a cell is exposed to a particular extracellular signal by virtue of the presence of cell surface proteins whose activities are affected by the extracellular protein.

B. Methods for the Delivery of DNA into Cells

A variety of methods for delivering nucleic acids, particularly large nucleic acid molecules, such as artificial chromosomes, including ACes (formerly designated SATACs), are provided. The methods generally involve exposing the nucleic acid molecule to an agent that increases contact between the nucleic acid molecule and the cell, and exposing the cell to a permeability enhancing agent. Each of the methods provided herein requires the use of one or both of these agents, which are applied in different orders, with the caveat that agents, such as energy, which increase the permeability of a cell, must be applied before contacting the cell with a nucleic acid.

In methods provided herein, large nucleic acid molecules are delivered using agents, including, but not limited to, delivery agents that enhance contact between the nucleic acid molecules and the cells and/or agents and treatments that increase cell permeability. Generally the nucleic acid molecules are delivered using agents that enhance contact between the nucleic acid and cells by neutralizing the charge of the nucleic acid molecules, and also by using energy to increase permeability of the cells. The agents may be used individually and in various combinations and orders of application, with the caveat that energy, such as sonoporation and electroporation cannot be applied to cells after the nucleic acid molecule is added thereto.

The method selected for delivering particular nucleic acid molecules, such as DNA, to targeted cells can depend on the particular nucleic acid molecule being transferred and the particular recipient cell. Preferred methods for particular nucleic acid molecules, such as DNA, and recipient cells are those that result in the greatest amount of nucleic acid molecules, such as DNA, transferred into the cell nucleus with an acceptable degree of cell survival. Suitable methods for delivery of particular pairings of nucleic acid molecules, such as DNA, and recipient cells may be determined using methods of monitoring nucleic acid molecules, such as DNA, delivery and methods of screening agents and conditions as provided herein or may be determined empirically using methods known to those of skill in the art.

The method selected requires consideration of a number of parameters, which are discussed in detail below. A method for detection of delivered nucleic acid is provided. This method, which can be used for assessing delivery of any nucleic acid molecule, can be used as a rapid screening tool to optimize chromosome transfer conditions.

In particular, delivery methods may first be assessed for the ability to transfer nucleic acid molecules, such as DNA, into cells and to identify methods that provide a sufficient number of viable cells that express the transferred nucleic acid molecules, such as DNA. Once such methods are identified, they may be optimized using the delivery monitoring methods provided herein and then assessed for the ability to provide for expression of the transferred nucleic acid molecules.

Delivery Agents

Delivery agents include compositions, conditions and physical treatments that enhance contact of nucleic acid molecules, such as DNA, with cells and/or increase the permeability of cells to nucleic acid molecules, such as DNA. Such agents include, but are not limited to, cationic compounds, peptides, proteins, energy, for example ultrasound energy and electric fields, and cavitation compounds.

Delivery agents for use in the methods provided herein include compositions, conditions or physical treatments to which cells and/or nucleic acid molecules, such as DNA, may be exposed in the process of transferring nucleic acid molecules, such as DNA, to cells in order to facilitate nucleic acid molecules, such as DNA, delivery into cells. For example, compounds and chemical compositions, including, but not limited to, calcium phosphate, DMSO, glycerol, chloroquine, sodium butyrate, polybrene and DEAE-dextran, peptides, proteins, temperature, light, pH, radiation and pressure are all possible delivery agents.

Cationic Compounds

Cationic compounds for use in the methods provided herein are available commercially or can be synthesized by those of skill in the art. Any cationic compound may be used for delivery of nucleic acid molecules, such as DNA, into a particular cell type using the provided methods. One of skill in the art by using the provided screening procedures can readily determine which of the cationic compounds are best suited for delivery of specific nucleic acid molecules, such as DNA, into a specific target cell type.

(a) Cationic Lipids

Cationic lipid reagents can be classified into two general categories based on the number of positive charges in the lipid headgroup; either a single positive charge or multiple positive charges, usually up to 5. Cationic lipids are often mixed with neutral lipids prior to use as delivery agents. Neutral lipids include, but are not limited to, lecithins; phosphatidylethanolamine; phosphatidyl-ethanolamines, such as DOPE (dioleoylphosphatidylethanolamine), DPPE (dipalmitoylphosphatidylethanolamine), POPE (palmitoyloleoylphosphatidyl-ethanolamine) and distearoylphosphatidylethanolamine; phosphatidylcholine; phosphatidylcholines, such as DOPC (dioleoylphosphatidylcholine), DPPC (dipalmitoylphosphatidylcholine), POPC (palmitoyloleoylphosphatidylcholine) and distearoylphosphatidylcholine fatty acid esters; glycerol esters; sphingolipids; cardiolipin; cerebrosides; and ceramides; and mixtures thereof. Neutral lipids also include cholesterol and other 3βOH-sterols.

Other lipids contemplated herein, include: phosphatidylglycerol; phosphatidylglycerols, such as DOPG (dioleoylphosphatidylglycerol), DPPG (dipalmitoylphosphatidylglycerol), and distearoyl-phosphatidylglycerol; phosphatidylserine; phosphatidylserines, such as dioleoyl- or dipalmitoylphosphatidylserine and diphosphatidylglycerols.

Examples of cationic lipid compounds include, but are not limited to: Lipofectin (Life Technologies, Inc., Burlington, Ont.)(1:1 (w/w) formulation of the cationic lipid N-[1(2,3-dioleyloxy)propyl]N,N,N-trimethylammonium chloride (DOTMA) and dioleoylphosphatidylethanolamine (DOPE); LipofectAMINE (Life Technologies, Burlington, Ont., see U.S. Pat. No. 5,334,761) (3:1 (w/w) formulation of polycationic lipid 2,3-dioleyloxy-N-[2(spermine-carboxamido) ethyl]-N,N-dimethyl-1-propanaminiumtrifluoroacetate (DOSPA) and dioleoylphosphatidylethanolamine (DOPE), LipofectAMINE PLUS (Life Technologies, Burlington, Ont. see U.S. Pat. Nos. 5,334,761 and 5,736,392; see, also U.S. Pat. No. 6,051,429) (LipofectAmine and Plus reagent), LipofectAMINE 2000 (Life Technologies, Burlington, Ont.; see also International PCT application No. WO 00/27795) (Cationic lipid), Effectene (Qiagen, Inc., Mississauga, Ontario) (Non liposomal lipid formulation), Metafectene (Biontex, Munich, Germany) (Polycationic lipid), Eu-fectins (Promega Biosciences, Inc., San Luis Obispo, Calif.) (ethanolic cationic lipids numbers 1 through 12: $C_{52}H_{106}N_6O_4.4CF_3CO_2H$, $CO_{88}H_{178}N_8O_4S_2.4CF_3CO_2H$, $C_{40}H_{84}NO_3P.CF_3CO_2H$, $C_{50}H_{103}N_7O_3.4CF_3CO_2H$, $C_{55}H_{116}N_8O_2.6CF_3CO_2H$, $C_{49}H_{102}N_6\ O_3.4CF_3CO_2H$, $C_{44}H_{89}N_5O_3.2CF_3CO_2H$, $C_{100}H_{206}N_{12}O_4S_2.8CF_3CO_2H$, $C_{162}H_{330}N_{22}O_9$. $13CF_3CO_2H$, $C_{43}H_{88}N_4O_2.2CF_3CO_2H$, $C_{43}H_{88}N_4O_3.2CF_3CO_2H$, $C_{41}H_{78}NO_8P$); Cytofectene (Bio-Rad, Hercules, Calif.) (mixture of a cationic lipid and a neutral lipid), GenePORTER (Gene Therapy Systems Inc., San Diego, Calif.) (formulation of a neutral lipid (Dope) and a cationic lipid) and FuGENE 6 (Roche Molecular Biochemicals, Indianapolis, Ind.) (Multi-component lipid based non-liposomal reagent).

(b) Non-Lipid Cationic Compounds

Non-lipid cationic reagents include, but are not limited to SUPERFECT™ (Qiagen, Inc., Mississauga, ON) (Activated dendrimer (cationic polymer:charged amino groups) and CLONfectin™ (Cationic amphiphile N-t-butyl-N'-tetradecyl-3-tetradecyl-aminopropionamidine) (Clontech, Palo Alto, Calif.).

Pyridinium amphiphiles are double-chained pyridinium compounds, which are essentially nontoxic toward cells and exhibit little cellular preference for the ability to transfect cells. Examples of a pyridinium amphiphiles are the pyridinium chloride surfactants such as SAINT-2 (1-methyl-4-(1-octadec-9-enyl-nonadec-10-enylenyl) pyridinium chloride) (see, e.g., van der Woude et al. (1997) *Proc. Natl. Acad. Sci. U.S.A.* 94:1160). The pyridinium chloride surfactants are typically mixed with neutral helper lipid compounds, such as dioleoylphosphatidylethanolamine (DOPE), in a 1:1 molar ratio. Other Saint derivatives of different chain lengths, state of saturation and head groups can be made by those of skill in the art and are within the scope of the present methods.

Energy

Delivery agents also include treatment or exposure of the cell and/or nucleic acid molecules, but generally the cells, to sources of energy, such as sound and electrical energy.

Ultrasound

For in vitro and in vivo transfection, the ultrasound source should be capable of providing frequency and energy outputs suitable for promoting transfection. Preferably, the output device can generate ultrasound energy in the frequency range of 20 kHz to about 1 MHz. The power of the ultrasound energy is preferably in the range from about 0.05 w/cm$^2$ to 2 w/cm$^2$, more preferably from about 0.1 w/cm$^2$ to about 1 w/cm$^2$. The ultrasound can be administered in one continuous pulse or can be administered as two or more intermittent pulses, which can be the same or can vary in time and intensity.

Ultrasound energy can be applied to the body locally or ultrasound-based extracorporeal shock wave lithotripsy can be used for "in-depth" application. The ultrasound energy can be applied to the body of a subject using various ultrasound devices. In general, ultrasound can be administered by direct contact using standard or specially made ultrasound imaging probes or ultrasound needles with or without the use of other medical devices, such as scopes, catheters and surgical tools, or through ultrasound baths with the tissue or organ partially or completely surrounded by a fluid medium. The source of ultrasound can be external to the subject's body, such as an ultrasound probe applied to the subject's skin which projects the ultrasound into the subject's body, or internal, such as a catheter having an ultrasound transducer which is placed inside the subject's body. Suitable ultrasound systems are known (see, e.g., International PCT application No. WO 99/21584 and U.S. Pat. No. 5,676,151).

When the cationic compound and nucleic acid molecules, such as DNA, are administered systemically, the ultrasound can be applied to one or several organs or tissues simultaneously to promote nucleic acid molecule delivery to multiple areas of the subject's body. Alternatively, the ultrasound can be applied selectively to specific areas or tissues to promote selective uptake of the nucleic acid molecules, such as DNA.

The transfection efficiency of the ultrasound can also be enhanced by using contrast reagents, which serve as artificial cavitation nuclei, such as Albunex (Molecular Biosystems, San Diego, Calif.), Imagent (Alliance Pharmaceutical, San Diego, Calif.), Levovist-SHU (Schering AG, Berlin, Germany), Definity (E.I. du Pont de Nemour, Wilmington, Del.), STUC (Washington University, St Louis, Mo.) and the introduction of gaseous microbubbles. A contrast reagent can be introduced locally, such as a joint; introduced systematically, with the enhancement of cavitation efficiency by focusing lithotripter shock waves at a defined area; or by targeting a contrast reagent to a particular site and then enhancing cavitation efficiency by focusing lithotripter shock waves.

Electroporation

Electroporation temporarily opens up pores in a cell's outer membrane by use of pulsed rotating electric fields. Methods and apparatus used for electroporation in vitro and in vivo are well known (see, e.g., U.S. Pat. Nos. 6,027,488, 5,993,434, 5,944,710, 5,507,724, 5,501,662, 5,389,069, 5,318,515). Standard protocols may be employed.

C. Target Cells and Delivery thereto

In Vitro Delivery

Cationic compounds and nucleic acid molecules, such as DNA, can be added to cells in vitro either separately or mixed together and with or without the application of ultrasound or electrical energy, as long as the energy is applied prior to contacting the cells with the nucleic acid molecule.

In general nucleic acid molecules, such as DNA, mixed with cationic lipids/compounds can be added to cell as described in the EXAMPLES. Parameters important for optimization of the delivery of nucleic acid molecules, such as DNA, into target cells will be apparent to those of skill in this art. These parameters include, for example, the cationic compound, cationic compound concentration, the nucleic acid molecules, such as DNA, the concentration of nucleic acid molecules, the cell growth medium, the cell culture conditions, the length of time cells are exposed to the cationic compound, the toxicity of the cationic compound to the target cell type, and the amount and time of use of ultrasound or electroporation among other parameters. It may be necessary to optimize these parameters for different nucleic acid molecules, such as DNA, and target cell types. Such optimization is routine employing the guidance provided herein. In addition, the rapid screening method can provide direction as to what parameters may need to be adjusted to optimize delivery (see EXAMPLES). Alteration of culture conditions, time, reagent concentrations and other parameters, for use with different combinations of cationic compounds and target cell types and to optimize delivery, can be empirically determined. If ultrasound energy is required to be used to enhance transfection efficiency, it can be applied as described below and in the EXAMPLES. Electroporation can be performed as described below or by any suitable protocol known to those of skill in this art.

The contacting of cells with cationic compounds and nucleic acid molecules, such as DNA, in separate and distinct steps can be generally carried out as described in the EXAMPLES. Those of skill in the art can readily vary the order of the application of the components to the target cell based on the disclosure herein.

Ex Vivo Gene Therapy

Delivery of nucleic acid molecules, such as DNA, is carried out as described above in in vitro delivery. After selection has been completed, cells harboring the nucleic acid molecules, such as DNA, are introduced into the subject target by a variety of means, including injection, such as subcutaneous, intramuscular, intraperitoneal, intravascular and intralymphatic injection. The cells can be administered with or without the aid of medical devices such as arthroscopes, other scopes or various types of catheters.

In Vivo Gene Therapy

In one method for delivering of the nucleic acid molecules, such as DNA, to target cells in the body of a subject in vivo, the cationic compound is first delivered to the target area (tissue, organ, tumor or joint). After waiting a suitable amount of time, the target area is then subjected to ultrasound frequency at a suitable energy level for a suitable time, which will be dependent on the equipment, tissue type and depth of the target area in the body. Alternatively, electrical energy is delivered to the target area. The nucleic acid molecules, such as DNA, is then delivered to the same area. Optionally, this procedure can be repeated so that the nucleic acid molecules, such as DNA, can be delivered via multiple injections over time or multiple administrations in different areas at the same time.

The cationic compound mixed together with the nucleic acid molecules, such as DNA, can be delivered to the target area. The target area is then subjected to ultrasound frequency at a suitable energy level for a suitable time. Depending on the nucleic acid molecules, such as DNA, the in vivo location, the cationic compound used and other variables, it may not be necessary to use ultrasound or electroporation to achieve suitable transfer efficiency to cells at the target area. Prior to the application of ultrasound, contrast reagents can be delivered to the target area to enhance transfer of the nucleic acid molecules, such as DNA.

The nucleic acid molecules, such as DNA, can be delivered to organs or tissues of the body such as skin, muscle, stomach, intestine, lung, bladder, ovary, uterus, liver, kidney, pancreas, brain, heart, spleen, prostate and joints (for example the knee, elbow, shoulder, wrist, hip, finger, and others. Molecules can be delivered to primary cell lines, such as fibroblast, muscle, stomach, intestine, lung, bladder, ovary, uterus, liver, kidney, pancreas, brain, heart, spleen, prostate to mimic in vivo systems.

The cationic compounds and the nucleic acid molecules, such as DNA, separately or together can be delivered to the target area of the body by a variety of means, including injection (for example, subcutaneous, intramuscular, intraperitoneal, intravascular and intralymphatic injection), instillation, cannulation, slow infusion, topical application and any other mode of administration. They can be administered by any suitable mode, including systemically (for example by intravenous injection), locally, such as by delivery to a specific target area (tissue or area), using, for example, a catheter or by direct injection. They can be administered with or without the aid of medical devices such as arthroscopes, other scopes or various types of catheters.

The cationic compounds can be administered also by coating a medical device, for example, a catheter, such as an angioplasty balloon catheter, with a cationic compound formulation. Coating may be achieved, for example, by dipping the medical device into a cationic lipid formulation or a mixture of a cationic compound formulation and a suitable solvent, for example, an aqueous-buffer, an aqueous solvent, ethanol, methylene chloride, chloroform and other suitable solvent. An amount of the formulation will naturally adhere to the surface of the device, which is subsequently administered to a subject, as appropriate. Alternatively, a lyophilized mixture of a cationic lipid formulation may be specifically bound to the surface of the device. Such binding techniques are known (see, e.g., Ishihara et al. (1993) *Journal of Biomedical Materials Research* 27:1309–1314).

The cationic compounds and nucleic acid molecules, such as DNA, can be formulated in pharmaceutically acceptable carriers, such as saline or other pharmaceutically acceptable solutions, for delivery in vivo. The nucleic acid molecules, such as DNA, and cationic compounds, regardless of the route of administration, are formulated into pharmaceutically acceptable dosage forms by standard methods known to those of skill in the art.

For gene therapy, the dosage level of the nucleic acid molecules, such as DNA, may be varied to achieve optimal therapeutic response for a particular subject. This depends on a variety of factors including mode of administration, activity of the nucleic acid molecules, such as DNA, characteristics of the protein produced, the transfection efficiency of the target cells (their ability to take up the nucleic acid molecules, such as DNA), the route of administration, the location of the target cells and other factors The dosage to be administered and the particular mode of administration will vary depending upon such factors as the age, weight and the particular animal and region thereof to be treated, the particular nucleic acid molecule and cationic compound used, the therapeutic or diagnostic use contemplated, and the form of the formulation, for example, suspension, emulsion, or liposomal, as will be readily apparent to those skilled in the art. Typically, dosage is administered at lower levels and increased until the desirable therapeutic effect is achieved. The amount of cationic compound that is administered can vary and generally depends upon the amount of nucleic acid molecules, such as DNA, being administered. For example, the weight ratio of cationic compound to nucleic acid molecules is preferably from about 1:1 to about 15:1, with a weight ratio of about 5:1 to about 1:1 being more preferred. Generally, the amount of cationic compound which is administered will vary from between about 0.1 milligram (mg) to about 1 gram (g). By way of general guidance, typically for a bodyweight of 70 kg and a composition with about 1 to 10 million chromosomes per ml, single dose ranging from 1 to 20 ml is administered as a single or repeated dose.

For localized treatment of diseases, such administration to affected joints in rheumatoid arthritis, psoriasis and diabetes should be possible, as well as injection into muscle for treatment of diseases, such as hemophilia or other genetic diseases. For other than local treatment a targeted delivery step is needed.

D. Assessing the Delivery of Nucleic Acid into Cells

Microscopic and colony formation analysis methods that may be used in evaluating stable nucleic acid molecule delivery rely on manual visualization or measurement of nucleic acid molecules (e.g., a selectable marker gene) expression, which is a distinct process from delivery. Such methods are associated with time delays in obtaining an assessment of the delivery method. Microscopic techniques for visualizing chromosome or plasmid transfer using bromodeoxyuridine (BrdU) (see. e.g., Pittman et al. *J Immunol Methods* 103:87–92 (1987)) are time consuming, restricted by the large sample size required to detect low levels of transfer and limited by the necessity of manual scoring. Colony-forming transfection analysis may require four-to-six weeks to generate and evaluate marker-expressing transfection colonies.

In contrast, methods provided herein are based on rapid, auto-mated, sensitive and accurate analysis procedures, such as flow cytometry, and thus do not involve any time-consuming, laborious and error-prone steps, such as manual detection of individual transfected cells by microscopic techniques. The methods make possible the analysis of nucleic acid molecule delivery data within 48 hours after transfection. Also, data collected by flow cytometry analysis is statistically superior due to the ease at which large numbers of events, e.g., nucleic acid molecule transfer, are collected. The positive values obtained in these methods are instrument derived and therefore not as susceptible to judgment errors. Thus, these methods provide for greater accuracy in assessing nucleic acid molecule delivery. In contrast, microscopic analysis is limited by the time involved for scoring positive events and sample size is restrictive.

Because the methods of monitoring nucleic acid molecule delivery detect labeled nucleic acid molecules, such as DNA, and not a reporter gene expression product, it is possible to measure absolute values of nucleic acid molecules transferred, within twenty-four hours, without being hindered by cell autofluorescence and by the problems of differentiating wild-type cells from cells expressing low levels of reporter gene products (see, e.g., Ropp et al. (1995) *Cytometry* 21:309–317).

1. Factors to Consider in Addressing Delivery of Nucleic Acids

Delivery of nucleic acids, including DNA, into cells is a process in which nucleic acids are transferred to the interior of a cell. Methods for the delivery of nucleic acids may be assessed in a variety of ways, including the following.

a. Transfer Efficiency

A delivery method may be assessed by determining the percentage of recipient cells in which the nucleic acids, including DNA, is present (i.e., the transfer efficiency). However, when evaluating a delivery method for the ultimate goal of generating cells that express the transferred nucleic acid, there are additional factors beyond mere presence of the nucleic acid in recipient cells that should be considered. Included among these additional factors is cell viability. When assessing a proliferating cell population, clonogenicity is the method of choice to measure viability. When the target cells population is non-dividing or slow growing, metabolic integrity can be monitored.

b. Clonogenicity

Clonogenicity represents a measure of the survivability of cells with respect to a delivery procedure, growth conditions and cell manipulations (e.g., plating). It is important to assess clonogenicity to determine whether a delivery procedure results in a sufficient number of viable cells to achieve a desired number of cells containing the transferred nucleic acid.

Clonogenicity may be expressed as a clonal fraction. The clonal fraction is an index that is calculated by multiplying two separate fractions and normalizing to a control plating efficiency correction factor (CPE). The two separate fractions that are multiplied in this calculation are the fraction of cells that survive a delivery procedure (population cell yield) and the fraction of cells that survive a plating procedure. The calculation is thus as follows:

$$\text{Colonal Fraction} = \frac{\text{\# viable colonies after plating}}{\text{\# cells plated}} \times \frac{\text{\# cells post-transfection}}{\text{\# cells transfected} \times CPE}$$

The values used in this calculation for the number of cells post-transfection (i.e., post-delivery) and the number of colonies post-plating is based on cell or colony numbers at certain times in the process. For instance, the value for the number of cells post-transfection is representative of the number of cells at a time after nucleic acid delivery that is sufficient for the delivery process to be completed. This time may be determined empirically. Typically this time ranges from 4–48 hours and generally is about one day after transfection. Likewise, the value of the number of viable colonies post-plating is representative of the number of colonies at a time after nucleic acid delivery that is sufficient for the non-viable cells to be eliminated and the viable cells to be established as colonies. This time may be determined empirically. Typically this time ranges from that in which the average colony is made up of approximately 50 cells or generally is a time at which five cell cycles have passed.

A correction factor is included to take into account the plating efficiency of control wells, which is the ratio determined by the number of colonies counted divided by the number cells initially plated (typically 600–1000 cells). For LM(tk-) and V79-4 cells, the value of the correction factor typically ranges from about 0.7 to about 1.2 and may be, for example, 0.9.

The number of cells plated should remain constant at 1000 (simplified plating efficiency assay) done in duplicate, except in the case where the CPE is below 0.3, then number of cells seeded should be increased to a range of 5,000–50,000. If the CPE is below 0.1–0.2, then a viable fraction analysis should be considered.

c. Viable Fraction

If the target cells population is non-dividing or slowly dividing then reproductive or clonogenicity assays are not relevant. Less direct measurements of cell viability must be used to measure cell killing that monitor metabolic death rather than loss of reproductive capacity. These procedures include, for example: (1) membrane integrity as measured by dye exclusion, (2) inhibition of nucleic acid synthesis as measured by incorporation of nucleic acid precursors, (3) radioactive chromium release, and (4) MTT ASSAY (3-[4,5-dimethylthiazol-2-yl]-2,5-diphenyl-tetrazolium bromide). These methods are different from measurements of loss of proliferative capacity, as they reflect only immediate changes in metabolism, which can be reversed or delayed and hence lead to errors in estimation of cell viability. To minimize these errors, correlation of duplicate procedures is suggested.

d. Potential Transfection Efficiency (PTE) and Determination of Chromos Index (CI)

In assessing a delivery method used to transfer nucleic acids to cells with the goal of expression of the nucleic acids, including DNA, therein, it is desirable to obtain an indication of the theoretical maximum percentage of cells that are viable and contain the nucleic acid out of the total number of cells into which nucleic acids were delivered. This is referred to as the potential transfection efficiency and may be calculated from existing or historical experimental data sets and is determined as follows:

Potential Transfection Efficiency (PTE)=Transfer Efficiency×(Clonal Fraction or Viable Fraction)×Correction Factor (CF)

The Chromos Index (C.I.) is an effective and rapid method to determine the Potential Transfection Efficiency of a proliferating population by using experimental values of % labeled nucleic acid, such as ACes, delivery to measure transfer efficiency and clonal fraction measured using a simplified clonogenicity assay.

Chromos Index (CI)=% labeled ACes delivery×estimated Clonal fraction×CF

The values of the transfer efficiency and of the clonal fraction and viable fraction are calculated as described above. The correction factor (CF) takes into account sample size, sample time and control plating efficiency. If all these factors are constant for each variable i.e., sampling time and size then the correction factor will approach the inverse of the value for the C.P.E., i.e., such that the clonal fraction or transfer efficiency can still approach 100% even with a low CF, or in other words, if delivery and viability are 100%, then the maximum potential transfection efficiency will equal the plating efficiency of the control cells. The calculation of C.I. allows for determination of each variable optimization, with the goal being for parameters, such as transfer efficiency, clonal fraction, and CF to approach one (or 100%). If sample size or time varies for either clonal fraction or transfer efficiency, then CF represents the extrapolated value based on slope or rate of change. An application of this assessment is provided in the EXAMPLES.

A stable transfection efficiency of about 1% is in the range (1–100%) that is considered useful for the introduction of large nucleic acid molecules into target cells. It is possible, using methods provided herein, to predict which delivery methods have to be selected for achieving desired transfection efficiencies without having to grow transfectants for extended times under selective conditions and determine numbers of cells surviving selection marker expression. This analysis involves calculation of the Chromos Index (CI) which integrates a "biological" value (the clonal fraction) with a measurement of chromosomal "uptake" or transfer efficiency (percentage of cells containing delivered ACes).

2. Labeling of Nucleic Acid Molecules for Transfer

In the methods for monitoring nucleic acid molecule delivery provided herein, the nucleic acid molecules, such as DNA, to be delivered are labeled to allow for detection of the nucleic acid molecules in recipient cells after transfer into the cells. The nucleic acid molecules may be labeled by incorporation of nucleotide analogs. Any nucleic acid molecule analog that may be detected in a cell may be used in these methods. The analog is either directly detectable, such as by radioactivity, or may be detected upon binding of a detectable molecule to the analog that specifically recognizes the analog and distinguishes it from nucleotides that make up the endogenous nucleic acid molecules, such as DNA, within a recipient cell. Analogs that are directly detectable have intrinsic properties that allow them to be detected using standard analytical methods. Analogs may also be detectable upon binding to a detectable molecule, such as a labeled antibody that binds specifically to the analogs. The label on the antibody is one that may be detected using standard analytical methods. For example, the antibody may be fluorescent and be detectable by flow cytometry or microscopy.

In particular embodiments of these methods, the nucleic acid molecules, such as DNA, to be transferred is labeled with thymidine analogs, such as Iododeoxyuridine (IdUrd) or Bromodeoxyuridine (BrdU). In preferred embodiments, IdUrd is used to label the nucleic acid molecules, such as DNA, to be transferred. The transferred IdUrd-labeled nucleic acid molecules, such as DNA, may be immunologically tagged using an FITC-conjugated anti-BrdU/IdUrd antibody and quantified by flow cytometry. Thus, the transfer of the labeled nucleic acid molecules, such as DNA, into recipient cells can be detected within hours after transfection.

E. Stability of Nucleic Acid Molecules to be Delivered

It is also of interest to evaluate the stability of the nucleic acid molecule, such as DNA, under the selected delivery conditions. Some delivery conditions and agents may have adverse effects on nucleic acid molecule structure. Furthermore, the labeling techniques used in certain methods of monitoring nucleic acid molecules, such as DNA, delivery may also impact nucleic acid molecules, such as DNA, structure and function.

The effects of delivery conditions on nucleic acid molecules may be assessed in a variety of ways, including microscopic analysis. In a particular exemplary analysis of the stability of artificial chromosomes, e.g., ACes, the chromosomes are exposed to the conditions of interest, e.g., IdU labeling, and analyzed under a fluorescent microscope for the ability to remain intact and condensed after incorporation of nucleotide analogs.

Methods of Monitoring Nucleic Acid Molecule Delivery and Expression

Methods of monitoring delivery of nucleic acid molecules delivery provided herein may also be combined with an assessment of nucleic acid molecule, such as DNA, expression in recipient cells to provide even further information concerning the overall process of nucleic acid molecule transfer for purposes of expression.

For example, to facilitate analysis of nucleic acid molecules, such as DNA, expression, it is desirable to include in the transferred nucleic acid molecules, such as DNA, a reporter gene that encodes a readily detected product. For direct detection, such reporter gene products include, but are not limited to green fluorescent proteins (GFP), Red Fluorescent protein (RFP), luciferases, and CAT. For indirect detection, reporter gene products include, but are not limited, to β-galactosidase and cell surface markers.

By using, for example, artificial chromosomes such as ACes containing a GFP reporter gene, such as, but are not limited to, GFP coding sequences in combination with labeling of the ACes with DNA analogs, such as IdU, delivery and expression can be rapidly and accurately monitored. For example, following the delivery of IdU-labeled GFP gene-containing ACes to target cells by any of the described methods, the cells containing the ACes are split into two populations. One population is fixed and stained for IdU and analyzed by flow cytometry to determine percentage delivery. The other population is allowed to go through 4–5 cell divisions (approximately 72 hours), and the GFP fluorescence is measured as an indication of expression.

Such studies have revealed that incorporation of the analog label does not affect GFP protein expression, which indicates that the methods may be combined to monitor delivery and early expression of the ACes, thus providing more information to rapidly evaluate the efficiency of delivery methods. The combined methods can also be used to map the biological events between the initial stages of delivery and early gene expression.

The following examples are included for illustrative purposes only and are not intended to limit the scope of the invention.

EXAMPLE 1

Preparation of Artificial Chromosomes

A. GFP Chromosome Contained in A9 Cell Line Plasmids

Plasmid pIRES-EGFP (see SEQ ID No. 13, plasmid obtained from Clontech, CA, and is well known, see, e.g., U.S. Pat. Nos. 6,034,228, 6,037,133, 5,985,577, 5,976,849, 5,965,396, 5,976,796, 5,843,884, 5,962,265, 5,965,396; see, also, U.S. Pat. No. 4,937,190). This plasmid contains the internal ribosome entry site (IRES; Jackson (1990) *Trends Biochem.* 15:477–483; Jang et al. (1988) *J. Virol.* 62:2636–2643) of the encephalomyocarditis virus (ECMV) between the MCS and the enhanced green fluorescent protein (EGFP) coding region. This permits the gene of interest (cloned into the MCS) and the EGFP gene to be translated from a single bicistronic mRNA transcript. Plasmid pIRES2-EGFP is designed for selection, by flow cytometry and other methods, of transiently transfected mammalian cells that express EGFP and the protein of interest. This vector can also be used to express EGFP alone or to obtain stably transfected cell lines without drug and clonal selection.

Enhanced GFP (EGFP) is a mutant of GFP with a 35-fold increase in fluorescence. This variant has mutations of Ser to Thr at amino acid 65 and Phe to Leu at position 64 and is encoded by a gene with optimized human codons (see, e.g., U.S. Pat. No. 6,054,312). EGFP is a red-shifted variant of wild-type GFP (Yang et al. (1996) *Nucl. Acids Res.* 24:4592–4593; Haas et al. (1996) *Curr. Biol.* 6:315–324; Jackson et al. (1990) *Trends Biochem.* 15:477–483) that has been optimized for brighter fluorescence and higher expression in mammalian cells (excitation maximum=488 nm; emission maximum=507 nm). EGFP encodes the GFPmut1 variant (Jackson (1990) *Trends Biochem.* 15:477–483) which contains the double-amino-acid substitution of Phe-64 to Leu and Ser-65 to Thr. The coding sequence of the EGFP gene contains more than 190 silent base changes which correspond to human codon-usage preferences (Jang et al. (1988) *J. Virol.* 62:2636–2643). Sequences flanking EGFP have been converted to a Kozak consensus translation initiation site (Huang et al. (1990) *Nucleic Acids Res.* 18: 937–947) to further increase the translation efficiency in eukaryotic cells.

Plasmid pIRES-EGFP was dervied from PIRESneo (orignally called pCIN4) by replacing the neo gene downstream of the IRES sequence with the EGFP coding region. The IRES sequence permits translation of two open reading frames from one mRNA transcript. The expression cassette of pIRES-EGFP contains the human cytomegalovirus (CMV) major immediate early promoter/enhancer followed by a multiple clonging site (MCS), a synthetic intron (IVS; Huang et al. (1990) *Nucleic Acids Res.* 18: 937–947), the EMCV IRES followed by the EGFP coding region and the polyadenylation signal of bovine growth hormone.

Location of Features (with reference to SEQ ID No. 13):

Human cytomegalovirus (CMV) immediate early promoter: 232-820;

MCS 909-974;

IVS 974-1269;

IRES of ECMV 1299-1884;

Enhanced green fluorescent protein (EGFP) gene 1905-2621;

fragment containing the bovine polyA signal 2636-2913;

Col E1 origin of replication 3343-4016; and

Amplicillin resistance gene 5026-4168

Propagation in E. coli

Suitable host strains: DH5a, HB101, and other general purpose strains. Single-stranded DNA production requires a host containing an F plasmid such as JM101 or XL1-Blue. Selectable marker: plasmid confers resistance to kanamycin (30 μg/ml) to E. coli hosts.
E. coli replication origin: pUC
Copy number: ~500
Plasmid incompatibility group: pMB1/ColE1 pCHEGFP2

Plasmid pCHEGFP2 was constructed by deletion of the NsiI/SmaI fragment from pIRES-EGFP. Plasmid pIRES-EGFP contains the coding sequence for a 2.1 kB Nru 1/Xho fragment of pCHEGFP2 containing the CMV promoter, synthetic intron, EGFP coding sequence and bovine growth hormone polyadenylation signal. Digestion of pIRES-EGFP with Nru 1 and Sma 1, yielded a 2.1 kb fragment. Digested DNA was fractionated by agarose gel electrophoresis, the separated band was excised and then eluted from the gel using the Qiaex 11 gel purification system (Qiagen, Mississauga, Ontario).

pFK161

Cosmid pFK161 was obtained from Dr. Gyula Hadlaczky and contains a 9 kb NotI insert derived from a murine rDNA repeat (see clone 161 described in PCT Application Publication No. WO97/40183 by Hadlaczky et al. for a description of this cosmid). This cosmid, referred to as clone 161 contains sequence corresponding to nucleotides 10,232–15,000 in SEQ ID NO. 16. It was produced by inserting fragments of the megachromosome (see, U.S. Pat. No. 6,077,697 and International PCT application No. (WO 97/40183); for example, H1D3, which was deposited at the European Collection of Animal Cell Culture (ECACC) under Accession No. 96040929, is a mouse-hamster hybrid cell line carrying this megachromosome) into plasmid pWE15 (Stratagene, La Jolla, Calif.) as follows. Half of a 100 μl low melting point agarose block (mega-plug) containing isolated SATACs was digested with NotI overnight at 37° C. Plasmid pWE15 was similarly digested with NotI overnight. The mega-plug was then melted and mixed with the digested plasmid, ligation buffer and T4 ligase. Ligation was conducted at 16° C. overnight. Bacterial DH5α cells were transformed with the ligation product and transformed cells were plated onto LB/Amp plates. Fifteen to twenty colonies were grown on each plate for a total of 189 colonies. Plasmid DNA was isolated from colonies that survived growth on LB/Amp medium and was analyzed by Southern blot hybridization for the presence of DNA that hybridized to a pUC19 probe. This screening methodology assured that all clones, even clones lacking an insert but yet containing the pWE15 plasmid, would be detected.

Liquid cultures of all 189 transformants were used to generate cosmid minipreps for analysis of restriction sites within the insert DNA. Six of the original 189 cosmid clones contained an insert. These clones were designated as follows: 28 (~9-kb insert), 30 (~9-kb insert), 60 (~4-kb insert), 113 (~9-kb insert), 157 (~9-kb insert) and 161 (~9-kb insert). Restriction enzyme analysis indicated that three of the clones (113, 157 and 161) contained the same insert.

For sequence analysis the insert of cosmid clone no. 161 was subcloned as follows. To obtain the end fragments of the insert of clone no. 161, the clone was digested with NotI and BamHI and ligated with NotI/BamHI-digested pBluescript KS (Stratagene, La Jolla, Calif.). Two fragments of the insert of clone no. 161 were obtained: a 0.2-kb and a 0.7-kb insert fragment. To subclone the internal fragment of the insert of clone no. 161, the same digest was ligated with BamHI-digested pUC19. Three fragments of the insert of clone no. 161 were obtained: a 0.6-kb, a 1.8-kb and a 4.8-kb insert fragment.

The insert corresponds to an internal section of the mouse ribosomal RNA gene (rDNA) repeat unit between positions 7551–15670 as set forth in GENBANK accession no. X82564, which is provided as SEQ ID NO. 5. The sequence data obtained for the insert of clone no. 161 is set forth in SEQ ID NOS. 6–12. Specifically, the individual subclones corresponded to the following positions in GENBANK accession no. X82564 (i.e., SEQ ID NO. 5) and in SEQ ID NOs. 6–12:

| Subclone | Start | End | Site | SEQ ID No. |
|---|---|---|---|---|
| | in X82564 | | | |
| 161k1 | 7579 | 7755 | NotI, BamHI | 6 |
| 161m5 | 7756 | 8494 | BamHI | 7 |
| 161m7 | 8495 | 10231 | BamHI | 8 (shows only sequence corresponding to nt. 8495–8950), 9 (shows only sequence corresponding to nt. 9851–10231) |
| 161m12 | 10232 | 15000 | BamHI | 10 (shows only sequence corresponding to nt. 10232–10600), 11 (shows only sequence corresponding to nt. 14267–15000) |
| 161k2 | 15001 | 15676 | NotI, BamHI | 12 |

The sequence set forth in SEQ ID NOs. 6–12 diverges in some positions from the sequence presented in positions 7551–15670 of GENBANK accession no. X82564. Such divergence may be attributable to random mutations between repeat units of rDNA.

For use herein, the rDNA insert from the clone was prepared by digesting the cosmid with NotI and Bg/II and was purified as described above. Growth and maintenance of bacterial stocks and purification of plasmids were performed using standard well known methods (see, e.g., Sambrook et al. (1989) *Molecular Cloning: A Laboratory Manual,* 2nd Edition, Cold Spring Harbor Laboratory Press), and plasmids were purified from bacterial cultures using Midi- and Maxi-preps Kits (Qiagen, Mississauga, Ontario).

B. Preparation of the GFP, Murine A9 Cell Line

Cell Culture and Transfection

The murine A9 cell line was obtained from ATCC and cells were thawed and maintained as described below. Briefly, cells were plated at a density of 2×10⁶ cells per 15 cm tissue culture dish (Falcon, Becton Dickinson Labware, Franklin Lakes, N.J.) in growth medium containing of 90% DMEM (Canadian Life Technologies Burlington, ON) and 10% FBS (Can Sera, Rexdale ON), and were maintained at 37° C., 5% $CO_2$. Cultures were routinely passaged when cells reached 70%–80% confluence. Sub culturing was carried out as follows: medium was removed by aspiration, 10 ml of 1× trypsin-EDTA (Canadian Life Technologies Burlington, ON) was dispensed onto the cell monolayer and the dish gently swirled to distribute the trypsin-EDTA. Finally, the bulk of the trypsin-EDTA was removed by aspiration, and the dish placed at 37° C. for 5 minutes. To quench the trypsin-EDTA, 10 ml of growth medium was added to the dish, and the single cell suspension was transferred to a 50 ml conical tube. Cell counts were performed using a cell counting apparatus (Beckman-Coulter, Hialeah Fla.). The cells were diluted and re-plated as described above. For cryo-storage, cultures were harvested by treatment with trypsin-EDTA, counted and the cell suspension then centrifuged at 500×g for 5 minutes in a swinging bucket centrifuge. The cell pellet was resuspended in freezing medium containing 90% DMEM, 20% FBS and 10% DMSO (Sigma-Aldrich, Oakville, ON) at a density of $1\times10^7$ cells/ml. One ml aliquots of the cell suspension were then dispensed into cryo-vials (Nunc, Rochester N.Y.), frozen over night in an isopropanol filled container (NUNC, Rochester N.Y.) and placed at −70° C. and then transferred to the gas phase of a liquid nitrogen freezer for long-term storage.

A9 cells were transfected using the $Ca_2PO_4$ co-precipitation method (see, e.g., Graham et al. (1978) *Virology* 52:456–457; Wigler et al. (1979) *Proc. Natl. Acad. Sci. U.S.A.* 76:1373–1376; and (1990) *Current Protocols in Molecular Biology*, Vol. 1, Wiley Inter-Science, Supplement 14, Unit 9.1.1–9.1.9). One day prior to transfection, A9 cells were plated at a density of $2\times10^6$ cells per 10 cm dish and 3 hours before transfection the medium was replaced with fresh growth medium. 140 μg of the 9 kb rDNA, NotI and 5 μg of the 2.1 kB CMV-EGFP XhoI/NruI fragments were mixed, co-precipitated and used to prepare the $Ca_2PO_4$ co-precipitate (Calcium Phosphate Transfection System, (Canadian Life Technologies Burlington, ON) which was distributed onto 2 10-cm dishes of subconfluent A9 cells. The DNA-$Ca_2PO_4$ complexes were left on the cells for 18 hours, after which the precipitate was removed by aspiration and cells were subjected to glycerol shock for 1.5 minutes. After glycerol shock, the cell monolayers were gently washed with 2×10 ml of dPBS (Canadian Life Technologies Burlington, ON), followed by addition of 10 ml pre-warmed growth medium. Finally dishes were returned to the incubator and were maintained at 37° C., 5% $CO_2$. After 3 hours recovery, each dish was passaged onto 3×15 cm tissue dishes GFP fluorescence of cultures was monitored visually during culture using an inverted microscope equipped with epifluorescence illumination (Axiovert 25; Zeiss, (North York ON) and #41017 Endow GFP filter set (Chroma Technologies, Brattleboro, Vt.). Enrichment of GFP expressing populations was carried out as described below.

Enrichment of GFP Expressing Cell Populations by Fluorescence Activated Cell Sorting Cell sorting was carried out using a FACS Vantage flow cytometer (Becton Dickinson Immunocytometry Systems, San Jose, Calif.) equipped with turbo-sort option and 2 Innova 306 lasers (Coherent, Palo Alto Calif.). For cell sorting a 70 μm nozzle was used. The sheath buffer was changed to PBS (maintained at 20 p.s.i.). GFP was excited with a 488 nm Laser beam and excitation detected in FL1 using a 500 EFLP filter. Forward and side scattering was adjusted to select for viable cells. Only viable cells were then analyzed for GFP fluorescence. Gating parameters were adjusted using wild type A9 cells as negative control and GFP CHO cells as positive control.

For the first round of sorting, A9 cells were harvested 4 days post-transfection, resuspended in 10 ml of growth medium and sorted for GFP expressing populations using parameters described above. GFP positive cells were dispensed into a volume of 5–10 ml of growth medium supplemented with 1× penicillin/streptomycin (Canadian Life Technologies Burlington, ON) while non-expressing cells were directed to waste. The expressing cells were further diluted to 50 ml using the same medium, plated onto 2×15 cm dishes and cultured as described in the previous section. When the sorted populations reached confluence they were re-sorted to enrich for GFP expressing cells. A total of 4 sequential sorts were carried out, achieving enrichments of as high as 89% GFP expressing cells after the final sort. The final GFP expressing populations were expanded for cryopreservation and for fluorescence in-situ hybridization screening (see below). Single cell clones were established from populations of interest by using the flow cytometer to direct GFP expressing single cells to individual wells of 96 well plates. These were cultured as described above.

Fluorescence In-Situ Hybridization

Fluorescence In-Situ Hybridization (FISH) screening was carried out on GFP enriched populations and single cell clones to detect amplification and/or artificial chromosome formation. Preparation of metaphase spreads and hybridizations were performed (see, Telenius et al. (1999) *Chromosome Res* 7:3–7). Probes used include pSAT 1, which recognizes the mouse major repeat (see, e.g., Wong et al. (1988) *Nucl. Acids Res.* 16:11645–11661), pFK161, which hybridizes to the mouse rDNA-containing regions and a PCR generated probe against the mouse minor repeat.

C. Purification of Artificial Chromosomes by Flow Cytometry and Preparation of DNA from Flow Sorted Chromosomes Artificial chromosomes were purified from the host cell by flow cytometry (see de Jong (1999) *Cytometry* 35:129–133). Briefly, purification was performed on FACS Vantage flow cytometer (Becton Dickinson Immunocytometry Systems, San Jose, Calif.) equipped with a Trubo-Sort Option and two Innova 306 lasers (Coherent, Palo Alto, Calif.). The Turbo Sort Option modification include increasing the maximum system pressure from 20 $lb/in^2$ to 60 $lb/in^2$, increasing the drop drive frequency from 50,000 drops/s to a maximum of 99,000 drops/s and increasing the deflection plate voltages from a maximum 6,000 V to 8,000 V. Other modifications are made to the instrument to accommodate the higher pressures. Hoechst 35258 was excited with the primary UV laser beam, and excitation detected in FL1 by using 420 nm hand-pass filter. Chromomycin A3 was excited by the second laser set at 458 nm and fluorescence detected in FL 4 by using a 475 nm long-pass filter. Both lasers had an output of 200 mW. Bivariate distributions (1,024×1024 channels) were accumulated during each sort. For all chromosome sorts, the sheath pressure was set at 30 $lb/in^2$ and a 50 μm diameter nozzle was installed. A drop delay profile was performed every morning and repeated after any major plug. Alignment of the instrument was performed daily by using 3.0 μm diameter Sphero rainbow beads (Spherotech, Libertyville, Ill.). Alignment was considered optimized when a CV of 2.0% or less was achieved for FL1 and FL4.

Condensing agents (hexylene glycol, spermine and spermidine) were added to the sheath buffer to maintain condensed chromosomes after sorting. The sheath buffer contains 15 nM Tris HCl, 0.1 mM EDTA, 20 mM NaCl, 1% hexylene glycol, 100 mM glycine, 20 μM spermine and 50 μM spermidine. The sorted chromosomes were collected in 1.5 ml screw-capped Eppendorf tubes at 4° C. at a concentration of approximately $1\times10^6$ chromosomes/ml, which were then stored at 4° C.

For preparation of purified genomic DNA, sorted chromosome samples were brought to 0.5% SDS, 50 mm EDTA and 100 μg/ml Proteinase K, then incubated for 18 hours at 50°0 C. 1 μl of a 20 mg/ml glycogen solution (Boehringer Mannheim) was added to each sample, followed by extraction with an equal volume of Phenol:Chloroform:Isoamyl Alcohol (25:24:1). After centrifugation at 21,000×g for 10 min, the aqueous phases were transferred to fresh microfuge tubes and were re-extracted as above. 0.2 volumes of 10 M $NH_4OAC$, 1 μl of 20 mg/ml glycogen and 1 volume of iso-propanol were added to the twice extracted aqueous phases which were then vortexed and centrifuged for 15 minutes at 30,000×g (at room temperature). Pellets were washed with 200 µl of 70% ethanol and re-centrifuged as above. The washed pellets were air-dried then resuspended in 5mM Tris-Cl, pH 8.0 at 0.5–2×10$^6$ chromosome equivalents/µl.

PCR was carried out on DNA prepared from sorted chromosome samples essentially as described (see, Co et al. (2000) *Chromosome Research* 8:183–191) using primers sets specific for EGFP and RAPSYN. Briefly, 50 µl PCR reactions were carried out on genomic DNA equivalent to 10,000 or 1000 chromosomes in a solution containing 10 mM Tris-Cl, pH 8.3, 50 mM KCl, 200 µM dNTPs, 500 nM of forward and reverse primers, 1.5 mM MgCl$_2$, 1.25 units Taq polymerase (Ampli-Taq, Perkin-Elmer Cetus, Calif.). Separate reactions were carried out for each primer set. The reaction conditions were as follows: one cycle of 10 min. at 95° C., then 35 cycles of 1 min. at 94° C., 1 min. at 55° C., 1 min at 72° C., and finally one cycle of 10 min at 72° C. After completion the samples were held at 4° C. until analyzed by agarose gel electrophoresis using the following primers (SEQ ID Nos. 1–4, respectively):
EGFP forward primer 5'-cgtccaggagcgcaccatcttctt-3';
EG FP reverse primer 3'-atcgcgcttctcgttggggtcrtt-3';
RAPSYN forward primer 5'-aggactgggtggcttccaactcccagacac-3'; and
RAPSYN reverse primer 5'-agcttctcattgctgcgcgccaggttcagg-3'.
All primers were obtained from Canadian Life Technologies, Burlington, ON.

EXAMPLE 2

Preparation of Cationic Vesicles

Vesicles were prepared at a lipid concentration of 700 nmol/ml lipid (cationic lipid/DOPE 1:1) as follows. In a glass tube (10 ml) 350 nmol cationic lipid (SAINT-2) was mixed with 350 nmol dioleoylphosphatidylethanolamine (DOPE), both solubilized in an organic solvent (Chloroform, Methanol or Chloroform/Methanol 1:1, v/v). Dioleoylphosphatidylethanolamine (DOPE; Avanti Polar Lipids, Alabaster, Ala.) forms inverse hexagonal phases in a membrane and weakens the membrane. Other effectors that may be used are cis-unsaturated phosphatidylethanolamines, cis-unsaturated fatty acids, and cholesterol. Cis-unsaturated phosphatidylcholines are less effective.

The solvent was evaporated under a stream of nitrogen (15 min/ 250 µl solvent at room temperature). The remaining solvent was removed totally by drying the lipid for 15 min in a desiccator under high vacuum from a vacuum pump. To the dried mixture was added 1 ml ultrapure water. This was vortexed vigorously for about 5 mm. The resulting solution was sonicated in an ultrasonication bath (Laboratory Supplies Inc. NY) until a clear solution was obtained. The resulting suspension contained a population of unilamellar vesicles with a size distribution between 50 to 100 nm.

EXAMPLE 3

Preparation of Cationic Vesicles via Alcoholic Injection

In a glass tube (10 ml) 350 nmol cationic lipid (Saint-2) was mixed with 350 nmol DOPE, both solubilized in an organic solvent (chloroform, methanol or chloroform/methanol 1/1). The solvent was evaporated under a stream of nitrogen (15 min/ 250 µl solvent at room temperature). The remaining solvent was removed totally by drying the lipid for 15 min under high vacuum. This was then reconstituted in 100 µl pure ethanol.

EXAMPLE 4

Transfection of Beta ACes into V79–4 Cell Line

Transfection Procedure for Various Transfection Agents

All compounds were tested in a Chinese Hamster lung fibroblast line (V79-4, ATCC number CCL-39). Approximately 17 hours (2 cell doublings) prior to transfection, exponentially growing cells were trypsinized and plated at 250,000 cells per well into a 6 well petri dish with Dulbecco's Modified Eagle Medium (Life Technologies, Burlington, ON) and supplemented with 10% FBS (Can Sera, Rexdale ON)). At the time of transfection, the number of cells per well was estimated to be approximately 1 million. For transfection, each individual manufacturer's protocol for complexing to naked DNA was followed, with the exception that the amount of transfection agent used was varied, to reflect the different amount and type of DNA present, as well as the different ionic strength of the complexing. One million ACes (in a volume of 800 µl) were typically combined with the transfection agent in a wide range of concentrations (between 5 times and 100 times the lowest manufacturers suggested concentration). The ACes/transfection mixture was allowed to complex for the time recommended by the manufacturer, in volumes ranging from 0.8 ml to 1.9 ml; some manufacturers recommend adding media to the complexing reaction. The complexed mixture was then applied to the recipient cells and transfection allowed to proceed according to the manufacturer's protocol. Details on the various conditions used with different agents are presented in Table 1.

Transfection Procedure for Superfect Agent

Superfect was tested in a Chinese Hamster lung fibroblast line (V79-4, ATCC number CCL-39). Approximately 17 hours (2 cell doublings) prior to transfection, exponentially growing cells were trypsinized and plated at 250,000 cells per well into a 6 well petri dish with Dulbecco's Modified Eagle Medium (Life Technologies, Burlington, ON) and supplemented with 10% FBS (Can Sera, Rexdale ON). One million ACes in 800 µl of sort buffer was complexed to 10 µl of Superfect reagent. Complex was incubated at room temperature for 10 minutes. At the time of transfection, the number of cells per well was estimated to be approximately 1 million. Media was removed from wells and 600 µl of DMEM and 10% FBS was added. Superfect:ACes complex was added to the wells drop-wise and allowed to incubate for 3 hours at 37° C. After incubation, transfected cells were trypsinized and transferred to 15 cm dishes with 25 ml DMEM and 10% FBS and allowed to attach for 24 hours. After 24 hours, selection medium containing of 0.7 mg/ml hygromycin B was added to each well. The selection medium was changed every 2–3 days. After 10–12 days colonies were screened for Beta-galactosidase expression and/or FISHed for detection of intact chromosome.

Example of Application of the Determination of the Chromos Index

Approximately 1×10$^6$ V79-4 cells were transfected with 1×10$^6$ IdUrd-labeled ACes complexed with a delivery agent (i.e., Lipofectamine PLUS and Lipofectamine or Superfect). The transfected cells were then fixed in ethanol. Fixed cells were denatured and exposed to FITC-conjugated antibody that specifically binds to BrdU/IdUrd-labeled nucleic acids.

The percentage of transfected cells containing IdUrd-labeled ACes was determined using flow cytometry and collecting FITC fluorescence. Data were accumulated to form bivariate channel distribution showing forward scatter versus green fluorescence (IdUrd-FITC). The fluorescence level at which cells were determined to be positive was established by visual inspection of the histogram of negative control cells such that the gate for the negative cells was set such that 1% appeared in the positive region.

The number of cells recovered at 24 hours post-transfection was determined by counting an aliquot using a Coulter Counter. To determine the control plating efficiency of a recipient cell line, the untreated cells were plated at 600–1000 cells per 10 cm petri dish in growth medium and left stationary in a 5% $CO_2$ incubator at 37° C. for approximately five cell cycles or until average colony was made up of 50 cells. At this point the number of viable colonies was determined. The treated cells were seeded at 1000 cells if the CPE is above 0.1–0.2. If the CPE is low then the seeding density is increased to 5,000–50,000 cells per dish.

EXAMPLE 5

Ultrasound Mediated Transfection of LMTK(-) Cells with Lipofectamine

LM(tk-) cells were grown at 37° C., 5% $CO_2$, in DMEM with 4500 mg/L D-glucose, L-glutamine, pyridoxine hydrochloride and 10% Fetal Bovine Serum. The corner wells of a 12-well dish were seeded with 200,000 cells per well (this is to ensure no interference from the ultrasound waves from other wells) 24 hours before use.

The GFP chromosomes were counted to verify approximately $1\times10^6$ ACes per ml. The chromosomes were resuspended in the tube by flicking. Ten µl of chromosome suspension was removed and mixed with an equal volume of 30 mg/ml PI (propidium iodide) stain. Eight µl of the stained chromosomes was loaded onto a Petroff Hausser counting chamber and the chromosomes were counted.

The medium was removed from the cells, and the cells were washed twice with HBSS (without phenol red, Gibco BRL) warmed to 37° C. 500 µl of the warmed HBSS was added to each well of cells (1 µl) LipofectAMINE (Gibco BRL) was added to each well. The plates were then sealed with parafilm tape and shaken gently at 20 rpm at room temperature for 30 minutes (Stagger plates—10 minutes for ease of handling).

After incubation Ultrasound gel (Other-Sonic Generic Ultra sound transmission gel, Pharmaceutical Innovations, Inc., Newark, N.J.) was applied to the 2.5 cm sonoporator head. Ultrasound was applied with an ImaRX Sonoporator 100 at an output energy of 2.0 Watt/cm2, for 60 seconds, through the bottom of the plate of cells. After ultrasound of the well one chromosome per seeded cell ($2\times10^5$) or 200 µl GFP ACes in sheath buffer (15 nM Tris HCl, 0.1 mM EDTA, 20 mM NaCl, 1% hexylene glycol, 100 mM glycine, 20 µM spermine and 50 µM spermidine) are added immediately to the well. (Repeat until all samples on the plate requiring ultrasound have been treated). The plate was then sealed once more with parafilm tape and shaken gently (20 rpm) for 1 hour at room temperature.

After the incubation 1 ml (DMEM with 4500 mg/L D-glucose, L-glutamine and pyridoxine hydrochloride, 10% Fetal Bovine Serum, and a 1× solution of penicillin and streptomycin from a 10000 units/ml penicillin and 10000 mg/ml Streptomycin, 100× stock solution) was added to each well and the cells were incubated 18–24 hours at 37° C.

The cells in the plates were then washed with antibiotic containing medium and 2 ml of medium was placed in each well. The cells continued to be incubated at 37° C. with 5% $CO_2$ until 48 hours after transfection/sonoporation. The cells were then trypsinised and resuspended at a concentration of $1\times10^6$ in DMEM to be analyzed by flow cytometry.

Results: Flow analysis was performed on a FACS Vantage (BDIS, San Jose, Calif.) equipped with a turbo-sort option and two Inova 305 lasers (Coherent, Palo Alto, Calif.). The GFP signal excitation is at 488 nm and the emission detected in FL1 using a 500 nm long pass filter. Analysis of the transfected cells generated populations of GFP positive cells ranging from 13–27%. Non-sonoporated control value was 5%.

EXAMPLE 6

Ultrasound Mediated Transfection with Saint-2

A. Ultrasound Mediated Transfection of CHO-KI Cells with Saint-2

CHO-KI cells were grown at 37°, 5% $CO_2$, in CHO-S-SFM 2 Medium, (Gibco BRL, Paisley, UK). Between $2\times10^5$ and $5\times10^5$ cells were plated onto sterile glass slides in a 12 well plate 24 h before usage.

Transfection of the cells was performed as follows. The medium was removed from the cells, and the cells were washed twice with HBSS (Hanks balanced salt solution without Phenol Red (Gibco BRL, UK)) at 37° C. Then 500 µl HBSS at 37° C. was added per well, followed by 10 µl of the freshly prepared vesicle solution (prepared in Example 2) to yield a final concentration of 23.3 nmol/ml.

Alternatively, the medium was removed from the cells, and the cells were washed twice with HBSS. 500 µl HBSS/lipid solution at 37° C. was added to each well. The HBSS/lipid solution was prepared by adding 1 µl ethanolic lipid solution (prepared as described above) to 500 µl HBSS under vigorous vortexing. The plates were then sealed with parafilm tape and shaken gently at room temperature for 30 min. After incubation, ultrasound was applied at an output energy of 0.5 Watt/cm² for 60 sec through the bottom of the plate to the cells. The ultrasound was mediated by an ultrasound gel (Aquasonic 100, Parker, N.J.) between transducer and plate. The ultrasound was applied with an ImaRx Sonoporator 100. Immediately after applying ultrasound one GFP chromosome per seeded cell ($2\times10^5$–$5\times10^5$) (prepared in Example 1) was added. The plate was then sealed again and shaken gently for 1 h at room temperature. After the incubation 1 ml medium (CHO—S—SFM 2 with 10% Fetal Calf Serum, 10000 µg/ml Penicillin and 10000 µg/ml Streptomycin Gibco BRL, Paisley, UK) was added to each well and the cells were incubated for 24 h at 37° C. The cells were then washed with medium, 1 ml medium was added, and the cells were incubated at 37° C. for another 24 h. Detection of expressed genes was then assayed by microscopy or detection of the transferred chromosome by FISH analysis. The negative control was performed in the same way, but with no chromosomes added to the cells.

Results

After transfection, using visual inspection, 30% of the cells remained on the glass slide of which 10% were positive for green fluorescent protein expression after 48 hours (3% of original population). After culturing for two weeks, FISH was performed on the cells and 1.4% of the cells contained an intact artificial chromosome.

B. Ultrasound Mediated Transfection of Hep-G2 Cells with Saint-2

Hep-G2 cells were grown at 37° C., 5% $CO_2$, in DMEM with 4500 mg/l Glucose, with Pyridoxine/HCl, 10% Fetal Calf Serum, 10000 μg/ml Streptomycin and 1000 μg/ml Penicillin. Between 2×10⁵ and 5×10⁵ cells were plated onto sterile glass slides in a 12 wells plate 24 hours before usage.

Cells were transfected with GFP chromosomes using the procedure of Example 6A except that the CHO-KI medium was replaced with Hep-G2 medium.

Results

After transfection, 30% of the cells remained on the glass slide. 80% of these cells were positive for green fluorescent protein expression.

C. Ultrasound Mediated Transfection of A9 Cells with Saint-2

A9 cells were grown at 37° C., 5% $CO_2$, in DMEM with 4500 mg/l Glucose, with Pyridoxine/HCl, 10% Fetal Calf Serum, 10000 μg/ml Streptomycin and 10000 μg/ml Penicillin (GIBCO BRL, Paisley, UK). Between 2×10⁵ and 5×10⁵ cells were plated onto sterile glass slides in a 12 well plate 24 h before usage.

Cells were transfected with GFP chromosomes using the procedure of Example 6A except that CHO-KI medium was replaced with A9 medium.

Results

After transfection, 30% of the cells remained on the glass of which 50% were positive for green fluorescent protein expression.

EXAMPLE 7

A Flow Cytometry Technique for Measuring Delivery of Artificial chromosomes

Production cells lines (see Example 1) were grown in MEM medium (Gibco BRL) with 10% fetal calf serum (Can Sera, Rexdale ON) with 0.168 μg/ml hygromycin B (Calbiochem, San Diego, Calif.). Iododeoxyurine or Bromodeoxyurdine were added directly to culture medium of the production cell line (CHO E42019) in the exponential phase of growth. Stock Iododeoxyurdine was made in tris base pH 10. Bromodeoxyurdine stocks in PBS. Final concentrations of 0.05–1 μM for continuous label of 20–24 hours of 5–50 μM with 15 minute pulse. After 24 hours, exponentially growing cells blocked in mitosis with colchicine (1.0 μg/ml for 7 hours before harvest. Chromosomes were then isolated and stained with Hoechst 33258 (2.5 μg/ml) and chromomycin A3 (50 μg/ml). Purification of artificial chromosomes was performed using a FACS Vantage flow cytometer (Becton Dickinson Immunocytometry systems, San Jose, Calif.). Chromomycin A3 was excited with the primary laser set at 457 nm, with emission detected using 475 nm long pass filter. Hoechst was excited by the secondary UV laser and emission detected using a 420/44 nm band-pass filter. Both lasers had an output of 150 mW.

Bivariate distribution showing cell karyotype was accumulated from each sort. ACes were gated from other chromosomes and sorted. Condensing agents (hexylene glycol, spermine, and spermidine) were added to the sheath buffer to maintain condensed intact chromosome after sorting. IdU labeling index of sorted chromosomes was determined microscopically. Aliquot (2–10 μl) of sorted chromosomes fixed in 0.2% formaldehyde solution for 5 minutes before being dried on clean microscopic slide. Microscope sample fixed with 70% ethanol. Air-dried slide denatured in coplin jar with 2N HCl for 30 minutes at room temperature and washed 2–3 times with PBS. Non specific binding was blocked with PBS and 4% BSA or serum for minimum of 10 minutes. A ⅕ dilution of FITC conjugated IdU/BrdU antibody (Becton Dickinson) with a final volume of 60–100 μl applied to slide. Plastic strips, Durra seal (Diversified Biotech, Boston, Mass.) were overlaid on slides, and slides kept in dark at 4% C in humidified covered box for 8–24 hours. DAPI (Sigma) 1 μg/ml in Vectorshield used as counterstain. Fluorescence detected using Zeiss axioplan 2 microscope equipped for epiflorescence. Minimum of 100 chromosomes scored for determining % labeled. Unlabeled chromosomes were used as negative control.

The day before the transfection, trypsinize V79-4 (Chinese Hamster Lung fibroblast) cells and plate at 250,000 into a 6 well petri dish in 4 ml DMEM (Dulbecco's Modified Eagle Medium, Life Technologies) and 10% FBS (Can Sera Rexdale ON). The protocol modified for use with LM (tk-) cell line by plating 500,000 cells. Lipid or dendrimer reagent was added to 1×10⁶ ACes sorted in ~800 μl sort buffer. Exemplary protocol variations are set forth in Table 1. Chromosome and transfection agents were mixed gently. Complexes were added to cells drop-wise and plate swirled to mix. Plates kept at 37° C. in a 5% $CO_2$ incubator for specified transfection time. The volume in a well was then made up to 4–5 ml with DMEM and 10% FBS. Recipient cells left for 24 hours at 37° C. in a 5% $CO_2$ incubator. Trypsinize transfected cells. Samples to be analyzed for IdU labeled chromosome delivery are fixed in cold 70% ethanol and stored at −20° C., to be ready for IdU antibody staining. Samples to be grown for colony selection are counted and then transferred to 10-cm dishes at densities of 10,000 and 100,000 cells in duplicate with remaining cells put in a 15 cm dish. After 24 hours, selection medium containing of DMEM and 10% FBS with 0.7 mg/ml hygromycin B, #400051 (Calbiochem San Diego, Calif.) is added. Selection medium is changed every 2–3 days. This concentration of hygromycin B kills the wild type cells after selection for 7 days. At 10–14 days colonies are expanded and then screened by FISH for intact chromosome transfer and assayed for beta galactosidase expression.

TABLE 1

Delivery Transfection Protocols

| Agent | Dilution Stock | Pre treatment of ACes | Complexing time (minutes) | Added to complexes | Medium (ml) added to wells before complexes | Transfection time (hours) |
|---|---|---|---|---|---|---|
| CLONFECTIN | 2–8 μg in NaCl-HEPES | | 20 | 1.8 ml of serum free | | 4 |
| CYTOFECTENE | | | 10–20 | 200 μl of 50% FBS plus DMEM | | 24 |
| ENHANCER + EFFECTENE (1:5 ratio) | | Enhancer 5 minutes | 10 | | 1.2 | 3 |

TABLE 1-continued

Delivery Transfection Protocols

| Agent | Dilution Stock | Pre treatment of ACes | Complexing time (minutes) | Added to complexes | Medium (ml) added to wells before complexes | Transfection time (hours) |
|---|---|---|---|---|---|---|
| EU-FECTIN-1 to 11 | | | 5–10 | | | 6 |
| FUGENE 6 | 0.5–6 µl to final volume of 100 µl in serum free medium | | 15–45 | | | 4 |
| GENEPORTER 2 | 2.5 µl added to 150 µl of serum free medium | | 2–10 | | | 2–4 |
| LIPOFECTAMINE | | | 15 | | | 3 |
| LIPOFECTAMINE 2000 | | | 20 | | 2.5 | 5 |
| METAFECTENE | diluted into 60 µl serum free medium | | 15–45 | | 0.8 | 6 |
| PLUS + LIPOFECTAMINE (1:1 and 3:2 ratio) | | PLUS and 200 µl of DMEM for 15 minutes | 15 | | | 3 |
| SUPERFECT | | | 10 | | 0.6 | 3 |

IDU Antibody Labeling

A standard BrdU staining flow cytometry protocol (Gratzer et al. Cytometry (1981);6:385–393) used except with some modifications at neutralization step, the presence of detergent during denaturation and the composition of blocking buffer. Between each step samples are centrifuged at 300 g for 7–10 minutes and supernatant removed. Samples of 1–2 million cells are fixed in 70% cold ethanol. Cells are then denatured in 1–2 ml of 2N HCl plus 0.5% triton X for 30 minutes at room temperature. Sample undergoes 3–4 washes with cold DMEM until indictor is neutral. Final wash with cold DMEM plus 5% FBS. Blocking/permeabilization buffer containing PBS, 0.1% triton X and 4% FBS is added for 10–15 minutes before pelleting sample by centrifugation. Add 20 µl of IdU/BrdU FITC conjugated B44 clone antibody (Becton Dickinson Immunocytometry Systems, San Jose, Calif.) to pellet and leave for 2 hours at room temperature in the dark with agitation every 30 minutes. Wash cells with block/permeabilization buffer and resuspend in PBS for flow analysis.

Flow Cytometry detection of Fluorescent IDUrd Labeled ACes

Percentage of transfected cells containing IdU labeled ACes was determined using a flow cytometry with an argon laser turned to 488 nm at 400 mW. FITC fluorescence was collected through a standard FITC 530/30-nm band pass filter. Cell populations were gated on the basis of side scatter versus forward scatter to exclude debris and doublets. Data were accumulated (15,000 events) to form bivariate channel distribution showing forward scatter versus green fluorescence (IdU-FITC). The fluorescence level at which cells were determined to be positive was established by visual inspection of the histogram of negative control cells, such that approximately 1% appeared in the positive region.

Results:

The transfection delivery results of IdU labeled ACes are set forth in Table 2.

TABLE 2

| COMPOUND | DOSE Microliters agent added per 1 | DELIVERY % IdU positive (24 hours) |
|---|---|---|
| CLONFECTIN | 6 | 0.61 |
| CYTOFECTENE | 8 | 14.67 |
| ENHANCER + EFFECTENE (1:5) | 1.6, 10 | 17.08 |
| EU-FECTIN-1 | 10 | 4.57 |
| EU-FECTIN-2 | 5 | 0.14 |
| EU-FECTIN-3 | 10 | 0.69 |
| EU-FECTIN-4 | 10 | 0.24 |
| EU-FECTIN-5 | 10 | 0.41 |
| EU-FECTIN-6 | 10 | 0.46 |
| EU-FECTIN-7 | 10 | 1.21 |
| EU-FECTIN-8 | 10 | 1.58 |
| EU-FECTIN-9 | 10 | 0.6 |
| EU-FECTIN-10 | 10 | 0.77 |
| EU-FECTIN-11 | 5 | 1 |
| FUGENE | 8 | 0.49 |
| GENEPORTER | 5 | 22.12 |
| LIPOFECTAMINE | 25 | 17.81 |
| LIPOFECTAMINE 2000 | 30 | 10.96 |
| PLUS + LIPOFECTAMINE (1:1) | 12, 12 | 12.2 |
| PLUS + LIPOFECTAMINE (3:2) | 24, 16 | 26.97 |
| METAFECTENE | 10 | 14.14 |
| SUPERFECT | 2 | 27.67 |

Since modifications will be apparent to those of skill in this art, it is intended that this invention be limited only by the scope of the appended claims.

What is claimed is:

1. A method for detecting or determining delivery and expression of nucleic acid introduced into a cell comprising:
   introducing labelled large nucleic acid molecules that encode a reporter gene into cells, wherein the labelled large nucleic acid is labelled with a label selected from the group consisting of a nucleotide analog, a nucleoside analog and a ribonucleoside analog;
   detecting labelled cells as an indication of delivery of the nucleic acid into a cell; and
   measuring the product of the reporter gene as an indication of DNA expression in the cell, whereby delivery and expression of nucleic acid molecules in the cell is detected or determined.

2. The method of claim 1, wherein the labelled cells are detected by flow cytometry, fluorimetry, cell imaging or fluorescence spectroscopy.

3. The method of claim 1, wherein the labelled cells are detected by flow cytometry.

4. The method of claim 1, wherein the nucleic acid molecule is DNA.

5. A method for detecting or determining delivery and expression of a nucleic acid introduced into a cell comprising:
   introducing labelled large nucleic acid molecules that encode a reporter gene into cells, wherein the label is iododeoxyuridine (IdU or IdUrd) or bromodeoxyuridine (BrdU);
   detecting labelled cells as an indication of delivery of the nucleic acid into a cell; and
   measuring the product of the reporter gene as an indication of DNA expression in the cell, whereby delivery and expression of nucleic acid molecules in the cell is detected or determined.

6. The method of claim 1, wherein the reporter gene encodes a fluorescent protein, or enzyme or antibody.

7. The method of claim 6, wherein the enzyme is a luciferase, β-galactosidase or alkaline phosphatase.

8. The method of claim 6, wherein the fluorescent protein is a red, green or blue fluorescent protein.

9. A method for detecting or determining delivery and expression of a nucleic acid introduced into a cell comprising:
- introducing labelled large nucleic acid molecules that encode a reporter gene into cells, wherein the step of introducing labelled large nucleic acid molecules comprises contacting the nucleic acid molecules with a delivery agent that comprises a cationic compound;
- detecting labelled cells as an indication of delivery of the nucleic acid into a cell; and
- measuring the product of the reporter gene as an indication of DNA expression in the cell, whereby delivery and expression of nucleic acid molecules in the cell is detected or determined.

10. The method of claim 9, wherein the compound is selected from the group consisting of N-[1-(2,3-dioleyloxy)propyl]-N,N,N-trimethylammonium chloride (DOTMA), dioleoylphosphatidylethanolamine (DOPE), 2,3-dioleyloxy-N-[2(spermine-carboxamido)ethyl]-N.N-dimethyl-1-propanaminiumtrifluoroacetate (DOSPA), $C_{52}H_{106}N_6O_4 \cdot 4CF_3CO_2H$, $C_{88}H_{178}N_8O_4S_2 \cdot 4CF_3CO_2H$, $C_{40}H_{84}NO_3P \cdot CF_3CO_2H$, $C_{50}H_{103}N_7O_3 \cdot 4CF_3CO_2H$, $C_{55}H_{116}N_8O_2 \cdot 6CF_3CO_2H$, $C_{49}H_{102}N_6O_3 \cdot 4CF_3CO_2H$, $C_{44}H_{89}N_5O_3 \cdot 2CF_3CO_2H$, $C_{41}H_{78}NO_8P$, $C_{100}H_{206}N_{12}O_4S_2 \cdot 6.8CF3CO_2H$, $C_{162}H_{330}N_{22}O_9 \cdot 13CF_3CF_3CO_2H$, $C_{43}H_{88}N_4O_2 \cdot 2CF_3CO_2H$, $C_{43}H_{88}N_4O_3 \cdot 2CF_3CO_2H$ and (1-methyl-4-(1-octadec-9-enyl-nonadec-10-enylenyl) pyridinium chloride.

11. The method of claim 1, wherein the nucleic acid molecules are natural chromosomes, artificial chromosomes, fragments of a chromosome or naked DNA that is greater than at least about 0.6 megabase in size.

12. The method of claim 1, wherein the nucleic acid molecules are artificial chromosomes, plasmids, chromosome fragments, naked DNA, or natural chromosomes.

13. The method of claim 1, wherein the nucleic acid molecules are artificial chromosome expression systems (ACes).

14. The method of claim 1, wherein the cells are eukaryotic cells.

15. The method of claim 1, wherein the cells are primary cells, cell lines, plant cells, or animal cells.

16. The method of claim 1, wherein the cells are stem cells, nuclear transfer donor cells, tumor cells or transformed cells.

17. The method of claim 1, wherein the cell is selected from the group consisting of a primary cell, an immortalized cell, an embryonic cell, a stem cell, a transformed cell and a tumor cell.

18. The method of claim 1, wherein the label is a thymidine analog.

* * * * *

UNITED STATES PATENT AND TRADEMARK OFFICE
CERTIFICATE OF CORRECTION

PATENT NO.      : 6,936,469 B2
DATED           : August 30, 2005
INVENTOR(S)     : Gary De Jong and Sandra Louise Vanderbyl It is certified that error appears in the above-identified patent and that said Letters Patent is hereby corrected as shown below:

Column 12,
Line 9, the formula "$CO_{88}H_{178}N_8O_4S_2.4CF_3CO_2H$" should read
-- $C_{88}H_{178}N_8O_4S_2.4CF_3CO_2H$ --.

Column 21,
Line 29, the phrase "SEQ ID NO. 16." should read -- SEQ ID NO. 16 of PCT Application Publication No. WO97/40183. --.

Column 61,
Lines 51-62, should read
-- 1. A method for detecting or determining delivery and expression of a nucleic acid introduced into a cell comprising:
   introducing labelled large nucleic acid molecules that encode a reporter gene into cells, wherein the labelled large nucleic acid is labelled with a label selected from the group consisting of a nucleotide analog, a nucleoside analog and a ribonucleoside analog;
   detecing labelled cells as an indication of delivery of the nucleic acid into a cell; and
   measuring the product of the reporter gene as an indication of DNA expression in the cell, whereby delivery and expression of nucleic acid molecules in the cell is detected or determined. --.

Column 63, line 17 - Column 64, line 2,
should read -- 10. The method of claim 9, wherein the compound is selected from the group consisting of N-[1-(2,3-dioleyloxy)propyl]-N,N,N-trimethylammonium chloride (DOTMA), dioleoylphosphatidylethanolamine (DOPE), 2,3-dioleyloxy-N-[2(spermine-carboxamido)ethyl]-N,N-dimethyl-1-propanaminiumtrifluoroacetate (DOSPA), $C_{52}H_{106}N_6O_4.4CF_3CO_2H$, $C_{88}H_{178}N_8O_4S_2.4CF_3CO_2H$, $C_{40}H_{84}NO_3P.CF_3CO_2H$, $C_{50}H_{103}N_7O_3.4CF_3CO_2H$, $C_{55}H_{116}N_8O_2.6CF_3CO_2H$,.$C_{49}H_{102}N_6O_3.4CF_3CO_2H$, $C_{44}H_{89}N_5O_3.2CF_3CO_2H$, $C_{41}H_{78}NO_8P$, $C_{100}H_{206}N_{12}O_4S_2.8CF_3CO_2H$, $C_{162}H_{330}N_{22}O_9.13CF_3CO_2H$, $C_{43}H_{88}N_4O_2.2CF_3CO_2H$, $C_{43}H_{88}N_4O_3.2CF_3CO_2H$ and (1-methyl-4-(1-octadec-9-enyl-nonadec-10-enylenyl-pyridinium chloride. --.

UNITED STATES PATENT AND TRADEMARK OFFICE
CERTIFICATE OF CORRECTION

PATENT NO. : 6,936,469 B2
DATED : August 30, 2005
INVENTOR(S) : Gary De Jong and Sandra Louise Vanderbyl It is certified that error appears in the above-identified patent and that said Letters Patent is hereby corrected as shown below:

<u>Column 64,</u>
Lines 15-20, should read:
-- 15. The method of claim 14, wherein the cells are primary cells, cell lines, plant cells, or animal cells.
   16. The method of claim 14, wherein the cells are stem cells, nuclear transfer donor cells, tumor cells or transformed cells. --.

Signed and Sealed this

Twenty-first Day of March, 2006

JON W. DUDAS
*Director of the United States Patent and Trademark Office*

SEQUENCE LISTING

<160> NUMBER OF SEQ ID NOS: 13

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
cgtccaggag cgcaccatct tctt                                              24

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
atcgcgcttc tcgttggggt cttt                                              24

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
aggactgggt ggcttccaac tcccagacac                                        30

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
agcttctcat tgctgcgcgc caggttcagg                                        30

<210> SEQ ID NO 5
<211> LENGTH: 22118
<212> TYPE: DNA
<213> ORGANISM: Mus musculus

<400> SEQUENCE: 5
gaattcccct atccctaatc cagattggtg gaataacttg gtatagatgt ttgtgcatta        60
aaaaccctgt aggatcttca ctctaggtca ctgttcagca ctggaacctg aattgtggcc       120
ctgagtgata ggtcctggga catatgcagt tctgcacaga cagacagaca gacagacaga       180
cagacagaca gacagacgtt acaaacaaac acgttgagcc gtgtgccaac acacacacaa       240
acaccactct ggccataatt attgaggacg ttgatttatt attctgtgtt tgtgagtctg       300
tctgtctgtc tgtctgtctg tctgtctgtc tatcaaacca aagaaaccaa acaattatg        360 cctgcctgcc tgcctgcctg cctacacaga gaaatgattt cttcaatcaa tctaaaacga       420
cctcctaagt ttgccttttt tctctttctt tatcttttc tttttctttt tcttcttcct       480
tccttccttc cttccttcct tccttccttt ctttctttct ttctttcttt cttactttct       540
ttctttcctt cttacatttta ttcttttcat acatagtttc ttagtgtaag catccctgac       600

-continued

```
tgtcttgaag acactttgta ggcctcaatc ctgtaagagc cttcctctgc ttttcaaatg      660
ctggcatgaa tgttgtacct cactatgacc agcttagtct tcaagtctga gttactggaa      720
aggagttcca agaagactgg ttatatttt catttattat tgcatttaa ttaaaattta       780
atttcaccaa aagaatttag actgaccaat tcagagtctg ccgtttaaaa gcataaggaa      840
aaagtaggag aaaaacgtga ggctgtctgt ggatggtcga ggctgcttta gggagcctcg      900
tcaccattct gcacttgcaa accgggccac tagaacccgg tgaagggaga aaccaaagcg      960
acctggaaac aataggtcac atgaaggcca gccacctcca tcttgttgtg cgggagttca     1020
gttagcagac aagatggctg ccatgcacat gttgtctttc agcttggtga ggtcaaagta     1080
caaccgagtc acagaacaag gaagtataca cagtgagttc caggtcagcc agagtttaca     1140
cagagaaacc acatcttgaa aaaacaaaa aataaatta aataaatata atttaaaaat       1200
ttaaaaatag ccgggagtga tggcgcatgt cttaatccc agctctcttc aggcagagat      1260
gggaggattt ctgagtttga ggccagcctg gtctgcaaag tgagttccag gacagtcagg     1320
gctatacaga gaaaccctgt cttgaaaact aaactaaatt aaactaaact aaactaaaaa     1380
aatataaaat aaaattta aagaatttta aaaaactaca gaaatcaaac ataagcccac       1440
gagatggcaa gtaactgcaa tcatagcaga aatattatac acacacac acacagactc      1500
tgtcataaaa tccaatgtgc cttcatgatg atcaaatttc gatagtcagt aatactagaa     1560
gaatcatatg tctgaaaata aaagccagaa cctttctgc ttttgtttc tttgcccca        1620
agatagggtt tctctcagtg tatccctggc atccctgcct ggaacttcct ttgtaggttt     1680
ggtagcctca aactcagaga ggtcctctct gcctgcctgc ctgcctgcct gcctgcctgc     1740
ctgcctgcct gcctgcctca cttcttctgc cacccacaca accgagtcga acctaggatc     1800
tttatttctt tctctttctc tcttctttct ttctttcttt cttctttct ttctttcttt     1860
cttctttct ttcttattca attagttttc aatgtaagtg tgtgttgtg ctctatctgc      1920
tgcctatagg cctgcttgcc aggagagggc aacagaacct aggagaaacc accatgcagc     1980
tcctgagaat aagtgaaaaa acaacaaaaa aaggaaattc taatcacata gaatgtagat     2040
atatgccgag gctgtcagag tgcttttta ggcttagtgt aagtaatgaa aattgttgtg      2100
tgtcttttat ccaaacacag aagagaggtg gctcggcctg catgtctgtt gtctgcatgt     2160
agaccaggct ggccttgaac acattaatct gtctgcctct gcttccctaa tgctgcgatt     2220
aaaggcatgt gccaccactg cccggactga tttcttcttt tttttttt tggaaaatac       2280
cttcttct ttttctctct ctctttcttc cttccttcct ttctttctat tcttttttc       2340
tttctttt cttttttt tttttttaa atttgccta aggttaaagg tgtgctccac           2400
aattgcctca gctctgctct aattctcttt aaaaaaaac aaacaaaaaa aaaaccaaaa      2460
cagtatgtat gtatgtatat ttagaagaaa tactaatcca ttaataactc ttttttccta    2520
aaattcatgt cattcttgtt ccacaaagtg agttccagga cttaccagag aaaccctgtg    2580
ttcaaatttc tgtgttcaag gtcaccctgg cttacaaagt gagttccaag tccgataggg    2640
ctacacagaa aaaccatatc tcagaaaaaa aaaagttcc aaacacacac acacacacac    2700
acacacacac acacacacac acacacacac acacacacag cgcgccgcgg cgatgagggg    2760
aagtcgtgcc taaaataaat attttctgg ccaaagtgaa agcaaatcac tatgaagagg     2820
tactcctaga aaaataaat acaaacgggc ttttaatca ttccagcact gttttaattt      2880
aactctgaat ttagtcttgg aaaaggggc gggtgtgggt gagtgagggc gagcgagcag     2940
```

```
acgggcgggc gggcgggtga gtggccggcg gcggtggcag cgagcaccag aaaacaacaa    3000
accccaagcg gtagagtgtt ttaaaaatga gacctaaatg tggtggaacg gaggtcgccg    3060
ccaccctcct cttccactgc ttagatgctc ccttcccctt actgtgctcc cttccctaa     3120 ctgtgcctaa ctgtgcctgt tccctcaccc cgctgattcg ccagcgacgt actttgactt    3180
caagaacgat tttgcctgtt ttcaccgctc cctgtcatac tttcgttttt gggtgcccga    3240
gtctagcccg ttcgctatgt tcgggcggga cgatgggac cgtttgtgcc actcgggaga     3300
agtggtgggt gggtacgctg ctccgtcgtg cgtgcgtgag tgccggaacc tgagctcggg    3360
agaccctccg gagagacaga atgagtgagt gaatgtggcg gcgcgtgacg gatctgtatt    3420
ggtttgtatg gttgatcgag accattgtcg ggcgacacct agtggtgaca agtttcggga    3480
acgctccagg cctctcaggt tggtgacaca ggagagggaa gtgcctgtgg tgaggcgacc    3540
agggtgacag gaggccgggc aagcaggcgg gagcgtctcg gagatggtgt cgtgtttaag    3600
gacggtctct aacaaggagg tcgtacaggg agatggccaa agcagaccga gttgctgtac    3660 gccctttgg gaaaaatgct agggttggtg gcaacgttac taggtcgacc agaaggctta     3720
agtcctaccc cccccccct tttttttttt tttcctccag aagccctctc ttgtcccgt      3780 caccgggggc accgtacatc tgaggccgag aggacgcgat gggcccggct tccaagccgg    3840
tgtggctcgg ccagctggcg cttcgggtct tttttttttt tttttttttt ttttcctcca    3900
gaagccttgt ctgtcgctgt caccgggggc gctgtacttc tgaggccgag aggacgcgat    3960 gggcccggc ttccaagccg gtgtggctcg gccagctgga gcttcgggtc ttttttttt      4020 tttttttttt tttttttctc cagaagcctt gtctgtcgct gtcaccgggg gcgctgtact    4080
tctgaggccg agaggacgcg atgggtcggc ttccaagccg atgtggcggg gccagctgga    4140
gcttcgggtt tttttttttc ctccagaagc cctctcttgt ccccgtcacc ggggcgctg     4200 tacttctgag gccagagga cgtgatgggc ccggttcca ggcggatgtc gcccggtcag      4260
ctggagcttt ggatcttttt tttttttttt cctccagaag ccctctcttg tccccgtcac    4320 cggggcacc ttacatctga gggcgagagg acgtgatggg tccggcttcc aagccgatgt     4380
ggcggggcca gctggagctt cgggtttttt tttttcctc cagaagccct ctcttgtccc     4440
cgtcaccggg ggcgctgtac ttctgaggcc gagaggacgt gatgggcccg gttccaggc     4500 ggatgtcgcc cggtcagctg gagctttgga tcatttttt ttttcctcc agaagccctc      4560 tcttgtcccc gtcaccgggg gcaccgtaca tctgaggccg agaggacacg atgggcctgt    4620
cttccaagcc gatgtggccc ggccagctgg agcttcgggt ctttttttt ttttttcctc    4680 cagaagcctt gtctgtcgct gtcaccgggg gcgctgtact tctgaggccg agaggacgcg    4740
atgggcccgg cttccaagcc ggtgtggctc ggccagctgg agcttcgggt cttttttttt    4800
tttttttttt ttcctccaga aaccttgtct gtcgctgtca cccggggcgc ttgtacttct    4860
gatgccgaga ggacgcgatg ggcccgtctt ccaggccgat gtggcccggt cagctggagc    4920
tttggatctt tttttttttt ttttcctcca gaagccctct cttgtcccg tcaccggggg     4980 caccttacat ctgaggccta gaggacacga tgggcccggg ttccaggccg atgtggcccg    5040
gtcagctgga gctttggatc ttttttttt ttttcttcca gaagccctct tgtccccgtc     5100
accggtggca ctgtacatct gaggcggaga ggacattatg ggcccggctt ccaatccgat    5160
gtggcccggt cagctggagc tttggatctt atttttttt taattttttc ttccagaagc     5220
cctcttgtcc ctgtcaccgg tggcacggta catctgaggc cgagaggaca ttatgggccc    5280
ggcttccagg ccgatgtggc ccggtcagct ggagctttgg atcttttttt ttttttttct    5340
```

```
tttttcctcc agaagccctc tctgtccctg tcaccggggg ccctgtacgt ctgaggccga      5400
gggaaagcta tgggcgcggt tttctttcat tgacctgtcg gtcttatcag ttctccgggt      5460
tgtcagggtc gaccagttgt tcctttgagg tccggttctt ttcgttatgg ggtcattttt      5520
gggccacctc cccaggtatg acttccaggc gtcgttgctc gcctgtcact ttcctccctg      5580
tctcttttat gcttgtgatc ttttctatct gttcctattg gacctggaga taggtactga      5640
cacgctgtcc tttccctatt aacactaaag gacactataa agagacccct tcgatttaag      5700
gctgttttgc ttgtccagcc tattcttttt actggcttgg gtctgtcgcg gtgcctgaag      5760
ctgtccccga gccacgcttc ctgctttccc gggcttgctg cttgcgtgtg cttgctgtgg      5820
gcagcttgtg acaactgggc gctgtgactt tgctgcgtgt cagacgtttt tcccgatttc      5880
cccgaggtgt cgttgtcaca cctgtcccgg ttggaatggt ggagccagct gtggttgagg      5940
gccaccttat ttcggctcac tttttttttt ttttttttctc ttggagtccc gaacctccgc      6000
tcttttctct tcccggtctt tcttccacat gcctcccgag tgcatttctt tttgttttttt      6060
ttctttttt tttttttttt ttggggaggt ggagagtccc gagtacttca ctcctgtctg      6120
tggtgtccaa gtgttcatgc cacgtgcctc ccgagtgcac tttttttttgt ggcagtcgct      6180
cgttgtgttc tcttgttctg tgtctgcccg tatcagtaac tgtcttgccc cgcgtgtaag      6240
acattcctat ctcgcttgtt tctcccgatt gcgcgtcgtt gctcactctt agatcgatgt      6300
ggtgctccgg agttctcttc gggccagggc caagccgcgc caggcgaggg acggacattc      6360
atggcgaatg gcggccgctc ttctcgttct gccagcgggc cctcgtctct ccaccccatc      6420
cgtctgccgg tggtgtgtgg aaggcagggg tgcggctctc cggcccgacg ctgccccgcg      6480
cgcactttc tcagtggttc gcgtggtcct tgtggatgtg tgaggcgccc ggttgtgccc      6540
tcacgtgttt cactttggtc gtgtctcgct tgaccatgtt cccagagtcg gtggatgtgg      6600
ccggtggcgt tgcatacccct tcccgtctgg tgtgtgcacg cgctgtttct tgtaagcgtc      6660
gaggtgctcc tggagcgttc caggtttgtc tcctaggtgc ctgcttctga gctggtggtg      6720
gcgctcccca ttccctggtg tgcctccggt gctccgtctg gctgtgtgcc ttcccgtttg      6780
tgtctgagaa gcccgtgaga gggggtcga ggagagaagg aggggcaaga ccccccttct      6840
tcgtcgggtg aggcgcccac cccgcgacta gtacgcctgt gcgtagggct ggtgctgagc      6900
ggtcgcggct ggggttggaa agtttctcga gagactcatt gctttcccgt ggggagcttt      6960
gagaggcctg gctttcgggg gggaccggtt gcagggtctc ccctgtccgc ggatgctcag      7020
aatgcccttg gaagagaacc ttcctgttgc cgcagacccc ccgcgcggt cgcccgcgtg      7080
ttggtcttct ggtttccctg tgtgctcgtc gcatgcatcc tctctcggtg gccggggctc      7140
gtcggggttt tgggtccgtc ccgccctcag tgagaaagtt tccttctcta gctatcttcc      7200
ggaaagggtg cgggcttctt acggtctcga ggggtctctc ccgaatggtc ccctggaggg      7260
ctcgccccct gaccgcctcc cgcgcgcgca gcgtttgctc tctcgtctac cgcggcccgc      7320
ggcctccccg ctccgagttc ggggagggat cacgcgggc agagcctgtc tgtcgtcctg      7380
ccgttgctgc ggagcatgtg gctcggcttg tgtggttggt ggctggggag agggctccgt      7440
gcacaccccc gcgtgcgcgt actttcctcc cctcctgagg gccgccgtgc ggacggggtg      7500
tgggtaggcg acgtgggct cccgggtccc caccccgtctt cccgtgcctc accccgtgcct      7560
tccgtcgcgt gcgtccctct cgctcgcgtc cacgactttg gccgctcccg cgacggcggc      7620
ctgcgccgcg cgtggtgcgt gctgtgtgct tctcgggctg tgtggttgtg tcgcctcgcc      7680
```

-continued

```
cccccttcc cgcggcagcg ttcccacggc tggcgaaatc gcgggagtcc tccttcccct    7740
cctcggggtc gagagggtcc gtgtctggcg ttgattgatc tcgctctcgg ggacgggacc    7800
gttctgtggg agaacggctg ttggccgcgt ccggcgcgac gtcggacgtg gggacccact    7860
gccgctcggg ggtcttcgtc ggtaggcatc ggtgtgtcgg catcggtctc tctctcgtgt    7920
cggtgtcgcc tcctcgggct cccgggggc cgtcgtgttt cgggtcggct cggcgctgca    7980
ggtgtggtgg gactgctcag gggagtggtg cagtgtgatt cccgccggtt ttgcctcgcg    8040
tgccctgacc ggtccgacgc ccgagcggtc tctcggtccc ttgtgaggac ccccttccgg    8100
gaggggcccg tttcggccgc ccttgccgtc gtcgccggcc ctcgttctgc tgtgtcgttc    8160
ccccctcccc gctcgccgca gccggtcttt tttcctctct cccccctct cctctgactg    8220 acccgtggcc gtgctgtcgg acccccgca tgggggcggc cgggcacgta cgcgtccggg    8280
cggtcaccgg ggtcttgggg gggggccgag gggtaagaaa gtcggctcgg cgggcgggag    8340
gagctgtggt ttggagggcg tcccggcccc gcggccgtgg cggtgtcttg cgcggtcttg    8400
gagagggctg cgtgcgaggg gaaaaggttg ccccgcgagg gcaaagggaa agaggctagc    8460
agtggtcatt gtcccgacgg tgtggtggtc tgttggccga ggtgcgtctg gggggctcgt    8520
ccggccctgt cgtccgtcgg gaaggcgcgt gttggggcct gccggagtgc cgaggtgggt    8580
accctggcgg tgggattaac cccgcgcgcg tgtcccggtg tggcggtggg ggctccggtc    8640
gatgtctacc tccctctccc cgaggtctca ggccttctcc gcgcgggctc tcggccctcc    8700
cctcgttcct ccctctcgcg gggttcaagt cgctcgtcga cctcccctcc tccgtccttc    8760
catctctcgc gcaatggcgc cgcccgagtt cacggtgggt tcgtcctccg cctccgcttc    8820
tcgccggggg ctggccgctg tccggtctct cctgcccgac cccgttggc gtggtcttct    8880 ctcgccggct tcgcggactc ctggcttcgc ccggagggtc agggggcttc ccggttcccc    8940
gacgttgcgc ctcgctgctg tgtgcttggg ggggcccgc tgcggcctcc gcccgcccgt    9000
gagcccctgc cgcacccgcc ggtgtgcggt ttcgcgccgc ggtcagttgg gccctggcgt    9060
tgtgtcgcgt cgggagcgtg tccgcctcgc ggcggctaga cgcgggtgtc gccgggctcc    9120
gacgggtggc ctatccaggg ctcgcccccg ccgaccccg cctgcccgtc ccggtggtgg    9180
tcgttggtgt ggggagtgaa tggtgctacc ggtcattccc tcccgcgtgg tttgactgtc    9240
tcgccggtgt cgcgcttctc tttccgccaa ccccacgcc aacccaccac cctgctctcc    9300
cggcccggtg cggtcgacgt tccggctctc ccgatgccga ggggttcggg atttgtgccg    9360
gggacggagg ggagagcggg taagagaggt gtcgagagc tgtcccgggg cgacgctcgg    9420
gttggctttg ccgcgtgcgt gtgctcgcgg acggttttg tcggacccg acggggtcgg    9480 tccgccgca tgcactctcc cgttccgcgc gagcgcccgc ccggctcacc cccggtttgt    9540
cctcccgcga ggctctccgc cgccgccgcc tcctcctcct ctctcgcgct ctctgtcccg    9600
cctggtcctg tcccaccccc gacgctccgc tcgcgcttcc ttacctggtt gatcctgcca    9660
ggtagcatat gcttgtctca aagattaagc catgcatgtc taagtacgca cggccggtac    9720
agtgaaactg cgaatggctc attaaatcag ttatggttcc tttggtcgct cgctcctctc    9780
ctacttggat aactgtggta attctagagc taatacatgc cgacgggcgc tgacccccct    9840
tcccgggggg ggatgcgtgc atttatcaga tcaaaaccaa cccggtgagc tccctcccgg    9900
ctccggccgg gggtcgggcg ccggcggctt ggtgactcta gataacctcg gccgatcgc    9960 acgcccccg tggcggcgac gacccattcg aacgtctgcc ctatcaactt tcgatggtag    10020
tcgccgtgcc taccatggtg accacgggtg acggggaatc agggttcgat tccggagagg    10080
```

```
gagcctgaga acggctacc acatccaagg aaggcagcag gcgcgcaaat tacccactcc    10140
cgacccgggg aggtagtgac gaaaaataac aatacaggac tctttcgagg ccctgtaatt   10200
ggaatgagtc cactttaaat cctttaacga ggatccattg gagggcaagt ctggtgccag   10260
cagccgcggt aattccagct ccaatagcgt atattaaagt tgctgcagtt aaaaagctcg   10320
tagttggatc ttgggagcgg gcgggcggtc cgccgcgagg cgagtcaccg cccgtccccg   10380
cccccttgcct ctcggcgccc cctcgatgct cttagctgag tgtcccgcgg ggcccgaagc   10440
gtttactttg aaaaaattag agtgttcaaa gcaggcccga gccgcctgga taccgcagct   10500
aggaataatg gaataggacc gcggttctat tttgttggtt ttcggaactg aggccatgat   10560
taagagggac ggccggggc attcgtattg cgccgctaga ggtgaaattc ttggaccggc   10620
gcaagacgga ccagagcgaa agcatttgcc aagaatgttt tcattaatca agaacgaaag   10680
tcggaggttc gaagacgatc agataccgtc gtagttccga ccataaacga tgccgactgg   10740
cgatgcggcg gcgttattcc catgacccgc cgggcagctt ccgggaaacc aaagtctttg   10800
ggttccgggg ggagtatggt tgcaaagctg aaacttaaag gaattgacgg aagggcacca   10860
ccaggagtgg gcctgcggct taatttgact caacacggga aacctcaccc ggcccggaca   10920
cggacaggat tgacagattg atagctcttt ctcgattccg tgggtggtgg tgcatggccg   10980
ttcttagttg gtggagcgat ttgtctggtt aattccgata acgaacgaga ctctggcatg   11040
ctaactagtt acgcgacccc cgagcggtcg gcgtccccca acttcttaga gggacaagtg   11100
gcgttcagcc accgagatt gagcaataac aggtctgtga tgcccttaga tgtccggggc   11160
tgcacgcgcg ctacactgac tggctcagcg tgtgcctacc ctgcgccggc aggcgcgggt   11220
aacccgttga accccattcg tgatgggat cggggattgc aattattccc catgaacgag   11280
gaattcccag taagtgcggg tcataagctt gcgttgatta agtccctgcc ctttgtacac   11340
accgcccgtc gctactaccg attggatggt ttagtgaggc cctcggatcg gccccgccgg   11400
ggtcggccca cggccctggc ggagcgctga aagacggtc gaacttgact atctagagga   11460
agtaaaagtc gtaacaaggt ttccgtaggt gaacctgcgg aaggatcatt aaacgggaga   11520
ctgtggagga gcggcggcgt ggcccgctct ccccgtcttg tgtgtgtcct cgccgggagg   11580
cgcgtgcgtc ccgggtcccg tcgcccgcgt gtggagcgag gtgtctggag tgaggtgaga   11640
gaagggggtgg gtggggtcgg tctgggtccg tctgggaccg cctccgattt cccctccccc   11700
tccctctcc ctcgtccggc tctgacctcg ccaccctacc gcggcggcgg ctgctcgcgg   11760
gcgtcttgcc tcttcccgt ccggctcttc cgtgtctacg aggggcggta cgtcgttacg   11820
ggtttttgac ccgtcccggg ggcgttcggt cgtcggggcg cgcgctttgc tctcccggca   11880
cccatccccg ccgcggctct ggcttttcta cgttggctgg ggcggttgtc gcgtgtgggg   11940
ggatgtgagt gtcgcgtgtg ggctcgcccg tcccgatgcc acgcttttct ggcctcgcgt   12000
gtcctccccg ctcctgtccc gggtacctag ctgtcgcgtt ccggcgcgga ggtttaagga   12060
ccccgggggg gtcgccctgc cgcccccagg gtcgggggc ggtggggccc gtagggaagt   12120
cggtcgttcg ggcggctctc cctcagactc catgaccctc ctcccccgc tgccgccgtt   12180
cccgaggcgg cggtcgtgtg gggggtggga tgtctggagc cccctcgggc gccgtggggg   12240
cccgacccgc gccgccggct tgcccgattt ccgcgggtcg gtcctgtcgg tgccggtcgt   12300
gggttcccgt gtcgttcccg tgttttttccg ctcccgaccc ttttttttttc ctccccccca   12360
cacgtgtctc gtttcgttcc tgctggccgg cctgaggcta cccctcggtc catctgttct   12420
```

-continued

```
cctctctctc cggggagagg agggcggtgg tcgttgggggg actgtgccgt cgtcagcacc   12480
cgtgagttcg ctcacacccg aaataccgat acgactctta gcggtggatc actcggctcg   12540
tgcgtcgatg aagaacgcag ctagctgcga gaattaatgt gaattgcagg acacattgat   12600
catcgacact tcgaacgcac ttgcggcccc gggttcctcc cggggctacg cctgtctgag   12660
cgtcggttga cgatcaatcg cgtcacccgc tgcggtgggt gctgcgcggc tgggagtttg   12720
ctcgcagggc caaccccccca acccgggtcg ggccctccgt ctcccgaagt tcagacgtgt   12780
gggcggttgt cggtgtggcg cgcgcgcccg cgtcgcggag cctggtctcc cccgcgcatc   12840
cgcgctcgcg gcttcttccc gctccgccgt tcccgccctc gcccgtgcac cccggtcctg   12900
gcctcgcgtc ggcgcctccc ggaccgctgc ctcaccagtc tttctcggtc ccgtgccccg   12960
tgggaaccca ccgcgccccc gtggcgcccg ggggtgggcg cgtccgcatc tgctctggtc   13020
gaggttggcg gttgagggtg tgcgtgcgcc gaggtggtgg tcggtcccct gcggccgcgg   13080
ggttgtcggg gtggcggtcg acgagggccg gtcggtcgcc tgcggtggtt gtctgtgtgt   13140
gtttgggtct tgcgctgggg gaggcgggggt cgaccgctcg cggggttggc gcggtcgccc   13200
ggcgccgcgc accctccggc ttgtgtggag ggagagcgag ggcgagaacg gagagaggtg   13260
gtatccccgg tggcgttgcg agggagggtt tggcgtcccg cgtccgtccg tccctccctc   13320
cctcggtggg cgccttcgcg ccgcacgcgg ccgctagggg cggtcggggc ccgtggcccc   13380
cgtggctctt cttcgtctcc gcttctcctt cacccgggcg gtacccgctc cggcgccggc   13440
ccgcgggacg ccgcggcgtc cgtgcgccga tgcgagtcac cccgggtgt tgcgagttcg   13500
gggagggaga gggcctcgct gacccgttgc gtcccggctt ccctgggggg gacccggcgt   13560
ctgtgggctg tgcgtccngg gggttgcgtg tgagtaagat cctccacccc cgccgccctc   13620
ccctcccgcc ggcctctcgg ggaccccctg agacggttcg ccggctcgtc ctcccgtgcc   13680
gccgggtgcc gtctctttcc cgcccgcctc ctcgctctct tcttcccgcg gctgggcgcg   13740
tgtccccccct ttctgaccgc gacctcagat cagacgtggc gacccgctga atttaagcat   13800
attagtcagc ggaggaaaag aaactaacca ggattccctc agtaacggcg agtgaacagg   13860
gaagagccca gcgccgaatc cccgccgcgc gtcgcggcgt gggaaatgtg gcgtacggaa   13920
gacccactcc ccggcgccgc tcgtgggggg cccaagtcct tctgatcgag gcccagcccg   13980
tggacggtgt gaggccggta gcggcccccgg cgcgccgggc tcgggtcttc ccggagtcgg   14040
gttgcttggg aatgcagccc aaagcgggtg gtaaactcca tctaaggcta aataccggca   14100
cgagaccgat agtcaacaag taccgtaagg gaaagttgaa aagaactttg aagagagagt   14160
tcaagagggc gtgaaaccgt taagaggtaa acgggtgggg tccgcgcagt ccgcccggag   14220
gattcaaccc ggcggcgcgc gtccggccgt gcccggtggt cccggcggat ctttcccgct   14280
ccccgttcct cccgacccct ccacccgcgc gtcgttcccc tcttcctccc cgcgtccggc   14340
gcctccggcg gcgggcgcgg ggggtggtgt ggtggtggcg cgcgggcggg gccggggtg   14400
gggtcggcgg gggaccgccc ccggccggcg accggccgcc gccgggcgca cttccaccgt   14460
ggcggtgcgc cgcgaccggc tccggacgg ccggaaggc ccggtgggga aggtggctcg   14520
ggggggggcgg cgcgtctcag ggcgcgccga accacctcac cccgagtgtt acagccctcc   14580
ggccgcgctt tcgccgaatc ccggggccga ggaagccaga tacccgtcgc cgcgctctcc   14640
ctctccccc gtccgcctcc cgggcgggcg tggggtggg ggccggggccg ccctcccac   14700
ggcgcgaccg ctctcccacc ccctccgtc gcctctctcg ggccggtgt ggggggcggg   14760
cggactgtcc ccagtgcgcc ccgggcgtcg tgcgccgtc gggtcccgg gggaccgtcg   14820
```

```
gtcacgcgtc tcccgacgaa gccgagcgca cggggtcggc ggcgatgtcg gctacccacc   14880
cgacccgtct tgaaacacgg accaaggagt ctaacgcgtg cgcgagtcag gggctcgtcc   14940
gaaagccgcc gtggcgcaat gaaggtgaag ggccccgccc gggggcccga ggtgggatcc   15000
cgaggcctct ccagtccgcc gagggcgcac caccggcccg tctcgcccgc cgcgccgggg   15060
aggtggagca cgagcgtacg cgttaggacc cgaaagatgg tgaactatgc ttgggcaggg   15120
cgaagccaga ggaaactctg gtggaggtcc gtagcggtcc tgacgtgcaa atcggtcgtc   15180
cgacctgggt ataggggcga aagactaatc gaaccatcta gtagctggtt ccctccgaag   15240
tttccctcag gatagctggc gctctcgctc ccgacgtacg cagttttatc cggtaaagcg   15300
aatgattaga ggtcttgggg ccgaaacgat ctcaacctat tctcaaactt taaatgggta   15360
agaagcccgg ctcgctggcg tggagccggg cgtggaatgc gagtgcctag tgggccactt   15420
ttggtaagca gaactggcgc tgcgggatga accgaacgcc gggttaaggc gcccgatgcc   15480
gacgctcatc agaccccaga aaaggtgttg gttgatatag acagcaggac ggtggccatg   15540
gaagtcggaa tccgctaagg agtgtgtaac aactcacctg ccgaatcaac tagccctgaa   15600
aatggatggc gctggagcgt cgggcccata cccggccgtc gccgcagtcg gaacggaacg   15660
ggacgggagc ggccgcgggt gcgcgtctct cggggtcggg ggtgcgtggc gggggcccgt   15720
cccccgcctc ccctccgcgc gccgggttcg ccccccgcgg gtcgggcccc gcggagccta   15780
cgccgcgacg agtaggaggg ccgctgcggt gagccttgaa gcctagggcg cgggcccggg   15840
tggagccgcc gcaggtgcag atcttggtgg tagtagcaaa tattcaaacg agaactttga   15900
aggccgaagt ggagaagggt tccatgtgaa cagcagttga acatgggtca gtcggtcctg   15960
agagatgggc gagtgccgtt ccgaagggac gggcgatggc ctccgttgcc ctcggccgat   16020
cgaaagggag tcgggttcag atccccgaat ccggagtggc ggagatgggc gccgcgaggc   16080
cagtgcggta acgcgaccga tcccggagaa gccggcggga ggcctcgggg agagttctct   16140
tttctttgtg aagggcaggg cgccctggaa tgggttcgcc ccgagagagg ggcccgtgcc   16200
ttggaaagcg tcgcggttcc ggcggcgtcc ggtgagctct cgctggccct tgaaaatccg   16260
ggggagaggg tgtaaatctc gcgccgggcc gtacccatat ccgcagcagg tctccaaggt   16320
gaacagcctc tggcatgttg gaacaatgta ggtaagggaa gtcggcaagc cggatccgta   16380
acttcgggat aaggattggc tctaagggct gggtcggtcg ggctggggcg cgaagcgggg   16440
ctgggcgcgc gccgcggctg gacgaggcgc cgccgcccte tcccacgtcc ggggagaccc   16500
cccgtccttt ccgcccgggc ccgccctccc ctcttcccg cggggccccg tcgtccccg    16560
cgtcgtcgcc acctctcttc cccctcctt cttcccgtcg gggggcgggt cggggtcgg    16620
cgcgcggcgc gggctccggg gcggcgggtc caacccccgcg ggggttccgg agcgggagga   16680
accagcggtc cccggtgggg cgggggcccc ggacactcgg ggggccggcg gcggcggcga   16740
ctctggacgc gagccgggcc cttcccgtgg atcgcctcag ctgcggcggg cgtcgcggcc   16800
gctcccgggg agcccggcgg gtgccggcgc gggtcccctc cccgcggggc ctcgctccac   16860
cccccatcg cctctcccga ggtgcgtggc ggggcgggg gggcgtgtcc cgcgcgtgtg     16920
gggggaacct ccgcgtcggt gttccccgc cgggtccgcc ccccgggccg cggttttccg    16980
cgcggcgccc ccgcctcggc cggcgcctag cagccgactt agaactggtg cggaccaggg   17040
gaatccgact gttttaattaa aacaaagcat cgcgaaggcc cgcggcgggt gttgacgcga   17100
tgtgatttct gcccagtgct ctgaatgtca aagtgaagaa attcaatgaa gcgcgggtaa   17160
```

-continued

```
acggcgggag taactatgac tctcttaagg tagccaaatg cctcgtcatc taattagtga   17220
cgcgcatgaa tggatgaacg agattcccac tgtccctacc tactatccag cgaaaccaca   17280
gccaagggaa cgggcttggc ggaatcagcg gggaaagaag accctgttga gcttgactct   17340
agtctggcac ggtgaagaga catgagaggt gtagaataag tgggaggccc ccggcgcccg   17400
gccccgtcct cgcgtcgggg tcggggcacg ccggcctcgc gggccgccgg tgaaatacca   17460
ctactctcat cgttttttca ctgacccggt gaggcggggg ggcgagcccc gagggctct    17520 cgcttctggc gccaagcgtc cgtcccgcgc gtgcgggcgg gcgcgacccg ctccggggac   17580
agtgccaggt ggggagtttg actggggcgg tacacctgtc aaacggtaac gcaggtgtcc   17640
taaggcgagc tcaggagga cagaaacctc ccgtggagca aagggcaaa agctcgcttg      17700 atcttgattt tcagtacgaa tacagaccgt gaaagcgggg cctcacgatc cttctgacct   17760
tttgggtttt aagcaggagg tgtcagaaaa gttaccacag ggataactgg cttgtggcgg   17820
ccaagcgttc atagcgacgt cgcttttttga tccttcgatg tcggctcttc ctatcattgt   17880
gaagcagaat tcaccaagcg ttggattgtt cacccactaa tagggaacgt gagctgggtt   17940
tagaccgtcg tgagacaggt tagttttacc ctactgatga tgtgttgttg ccatggtaat    18000
cctgctcagt acgagaggaa ccgcaggttc agacatttgg tgtatgtgct tggctgagga   18060
gccaatgggg cgaagctacc atctgtggga ttatgactga acgcctctaa gtcagaatcc   18120
gcccaagcgg aacgatacgg cagcgccgaa ggagcctcgg ttggccccgg atagccgggt   18180
ccccgtccgt cccgctcggc ggggtccccg cgtcgcccg cggcggcgcg gggtctcccc     18240
ccgccgggcg tcgggaccgg ggtccggtgc ggagagccgt tcgtcttggg aaacggggtg   18300
cggccggaaa gggggccgcc ctctcgcccg tcacgttgaa cgcacgttcg tgtggaacct   18360
ggcgctaaac cattcgtaga cgacctgctt ctgggtcggg gtttcgtacg tagcagagca    18420
gctccctcgc tgcgatctat tgaaagtcag ccctcgacac aagggtttgt ctctgcgggc   18480
tttcccgtcg cacgcccgct cgctcgcacg cgaccgtgtc gccgcccggg cgtcacgggg   18540
gcggtcgcct cggcccccgc gcggttgccc gaacgaccgt gtggtggttg ggggggggat    18600
cgtcttctcc tccgtctccc gaggacggtt cgtttctctt tccccttccg tcgctctcct   18660
tgggtgtggg agcctcgtgc cgtcgcgacc gcggcctgcc gtcgcctgcc gccgcagccc   18720
cttgccctcc ggccttggcc aagccggagg gcggaggagg gggatcggcg gcggcggcga   18780
ccgcggcgcg gtgacgcacg gtgggatccc catcctcggc gcgtccgtcg gggacggccg   18840
gttggagggg cgggagggt ttttcccgtg aacgccgcgt tcggcgccag gcctctggcg    18900
gccggggggg cgctctctcc gcccgagcat ccccactccc gcccctcctc ttcgcgcgcc   18960
gcggcggcga cgtgcgtacg aggggaggat gtcgcggtgt ggaggcggag agggtccggc   19020
gcggcgcctc ttccattttt tcccccccaa cttcggaggt cgaccagtac tccgggcgac   19080
actttgtttt ttttttttcc cccgatgctg gaggtcgacc agatgtccga aagtgtcccc   19140
cccccccccc cccccggcg cggagcggcg gggccactct ggactctttt tttttttttt   19200
tttttttttt ttaaattcct ggaacctta ggtcgaccag ttgtccgtct tttactcctt     19260
catataggtc gaccagtact ccgggtggta ctttgtcttt ttctgaaaat cccagaggtc   19320
gaccagatat ccgaaagtcc tctctttccc tttactcttc cccacagcga ttctcttttt   19380
tttttttttt tttggtgtgc ctctttttga cttatataca tgtaaatagt gtgtacgttt   19440
atatacttat aggaggaggt cgaccagtac tccgggcgac actttgtttt tttttttttt   19500
tccaccgatg atggaggtcg accagatgtc cgaaagtgtc ccgtcccccc cctccccccc   19560
```

```
ccgcgacgcg gcgggctcac tctggactct tttttttttt tttttttttt tttaaatttc   19620 tggaaccttaaggtcgaccagttgtccgtctttcactcattcatataggtcgaccggtgg19680 tactttgtct ttttctgaaa atcgcagagg tcgaccagat gtcagaaagt ctggtggtcg   19740 ataaattatctgatctagatttgttttttctgttttttcagttttgtgttgttttgtgttgt19800 tttgtgttgt tttgtttgt tttgtttgt tttgttttgt tttgttttgt tttgttttgt   19860 tttgtgttgtgttgtgttgtgttgtgttggttgggttgggttgggttgggttgggttgg19920 gttgggttgggttgggttgttgttgtttggtttgtgttgtttggtgttgttggttttgtt19980 ttgtttgctg ttgttttgtg ttttgcgggt cgaacagttg tccctaaccg agttttttg   20040 tacacaaaca tgcactttt ttaaaataaa tttttaaaat aaatgcgaaa atcgaccaat   20100
tatccctttc cttctctctc tttttaaaa attttctttg tgtgtgtgtg tgtgtgtgtg   20160
tgtgtgtgtg tgcgtgtgtg tgtgtgtgtg cgtgcagcgt gcgcgcgctc gttttataaa   20220
tacttataat aataggtcgc cgggtggtgg tagcttcccg gactccagag gcagaggcag   20280
gcagacttct gagttcgagg ccagcctggt ctacagagga accctgtctc gaaaatgaa   20340 aataaataca tacatacata catacatata tacatacata catacatata tacatatgag   20400
gttgaccagt tgtcaatcct ttagaatttt gttttaatt aatgtgatag agagatgat   20460 aatagataga tggatagagt gatacaaata taggttttt tttcagtaaa tatgaggttg   20520
attaaccact ttccccttt taggtttttt ttttttttccc ctgtccatgt ggttgctggg   20580
atttgaactc aggaccctgg caggtcaact ggaaaacgtg tttctatat atataaatag   20640 tggtctgtct gctgttttt tgtttgcttg cttgcttgct tgcttgcttg cttgcttgct   20700 tgctttttt tttcttctga acagtatt ctctgtgtaa cctggtgccc tgaaactcac   20760
tctgtagacc agcctggcct caatcgaact cagaaatcct cctgcctctt gtctacctcc   20820 caatttgga gtaaaggtgt gctacaccac tgcctggcat tattatcatt atcattatta   20880 atttatattag acagaac gaaatcaact agttggtcct gtttcgttaa ttcatttgaa   20940
attagttgga ccaattagtt ggctggttg ggaggtttct tttgtttccg atttggtgt   21000 ttgtgggct ggggatcagg tatctcaacg gaatgcatga aggttaaggt gagatggctc   21060
gatttttgta aagattactt tcttagtct gaggaaaaaa taaataata ttgggctacg   21120 tttcattgct tcatttctat ttctctttct ttctttcttt cttcagata aggaggtcgg   21180 ccagttcctc ctgccttctg gaagatgtag gcattgcatt gggaaagca ttgtttgaga   21240 gatgtgctag tgaaccagag agtttggatg tcaagccgta taatgtttat tacaatatag   21300
aaaagttcta acaaagtgat ctttaactt tttttttttt ttctccttc tacttctact   21360 tgttctcact ctgccaccaa cgcgctttgt acattgaatg tgagctttgt tttgcttaac   21420
agacatatat ttttttcttt ggtttgctt gacatggttt ccctttctat ccgtgcaggg   21480
ttcccagacg gcctttgag aataaaatgg gaggccagaa ccaaagtctt ttgaataaag   21540
caccacaact ctaacctgtt tggctgtttt ccttcccaag gcacagatct ttcccagcat   21600
ggaaaagcat gtagcagttg taggacacac tagacgagag caccagatct cattgtgggt   21660
ggttgtgaac cacccaccat gtggttgcct gggatttgaa ctcaggatct tcagaagacg   21720
agtcagggct ctaaaccgat gagccatctc tccagccctc ctacattcct tcttaaggca   21780
tgaatgatcc cagcatggga agacagtctg ccctctttgt ggtatatcac catatactca   21840
ataaaataat gaaatgaatg aagtctccac gtatttattt cttcgagcta tctaaattct   21900
```

-continued

```
ctcacagcac ctcccctcc cccacactgc cttctcct atgtttgggt ggggctgggg      21960 gagggtggg gtgggggcag ggatctgcat gtcttcttgc aggtctgtga actatttgcg     22020
atggcctggt tctctgaact gttgagcctt gtctatccag aggctgactg gctagttttc    22080
tacctgaagt ccctgagtga tgatttccct gtgaattc                            22118
```

<210> SEQ ID NO 6
<211> LENGTH: 175
<212> TYPE: DNA
<213> ORGANISM: Mus Musculus

<400> SEQUENCE: 6

```
ctcccgcgcg gcccccgtgt tcgccgttcc cgtggcgcgg acaatgcggt tgtgcgtcca      60
cgtgtgcgtg tccgtgcagt gccgttgtgg agtgcctcgc tctcctcctc ctccccggca     120
gcgttcccac ggttggggac caccggtgac ctcgccctct tcgggcctgg atccg          175
```

<210> SEQ ID NO 7
<211> LENGTH: 755
<212> TYPE: DNA
<213> ORGANISM: Mus musculus

<400> SEQUENCE: 7

```
ggtctggtgg gaattgttga cctcgctctc gggtgcggcc tttggggaac ggcggggtcg      60
gtcgtgcccg gcgccggacg tgtgtcgggg cccacttccc gctcgagggt ggcggtggcg     120
gcggcgttgg tagtctcccg tgttgcgtct tcccgggctc ttggggggggg tgccgtcgtt    180 ttcgggccg gcgttgcttg gcttacgcag gcttggtttg ggactgcctc aggagtcgtg     240
ggcggtgtga ttcccgccgg ttttgcctcg cgtctgcctg ctttgcctcg ggtttgcttg    300
gttcgtgtct cgggagcggt ggtttttttt tttttcgggt cccggggaga ggggttttc    360 cgggggacgt tcccgtcgcc ccctgccgcc ggtgggttt cgtttcgggc tgtgttcgtt    420
tccccttccc cgtttcgccg tcggttctcc ccggtcggtc ggccctctcc ccggtcggtc    480
gcccggccgt gctgccggac ccccccttct ggggggatg cccgggcacg cacgcgtccg    540
ggcggccact gtggtccggg agctgctcgg caggcgggtg agccagttgg aggggcgtca    600 tgccccgcg ggctcccgtg gccgacgcgg cgtgttcttt gggggggcct gtgcgtgcgg    660
gaaggctgcg cacgttgtcg gtccttgcga gggaagagg cttttttttt ttaggggggtc    720 gtccttcgtc gtcccgtcgg cggtggatcc ggcct                               755
```

<210> SEQ ID NO 8
<211> LENGTH: 463
<212> TYPE: DNA
<213> ORGANISM: Mus musculus

<400> SEQUENCE: 8

```
ggccgaggtg cgtctgcggg ttggggctcg tccggccccg tcgtcctccg ggaaggcgtt      60
tagcgggtac cgtcgccgcg ccgaggtggg cgcacgtcgg tgagataacc ccgagcgtgt    120 ttctggtttgt tggcggcggg ggctccggtc gatgtcttcc cctccccctc tcccgaggc    180 caggtcagcc tccgcctgtg ggcttcgtcg gccgtctccc ccccctcac gtccctcgcg    240 agcgagcccg tccgttcgac cttccttccg ccttccccc atctttccgc gctccgttgg    300
ccccggggtt ttcacggcgc ccccacgct cctccgcctc tccgccgtg gtttggacgc    360 ctggttccgg tctccccgcc aaaccccggt tgggttggtc tccggccccg gcttgctctt    420
cgggtctccc aacccccggc cggaagggtt cggggggttcc ggg                     463
```

<210> SEQ ID NO 9
<211> LENGTH: 378
<212> TYPE: DNA
<213> ORGANISM: Mus musculus

<400> SEQUENCE: 9

```
ggattcttca ggattgaaac ccaaaccggt tcagtttcct ttccggctcc ggccggggg     60
ggcggccccg ggcggtttgg tgagttagat aacctcgggc cgatcgcacg ccccccgtgg    120
cggcgacgac ccattcgaac gtctgcccta tcaactttcg atggtagtcg atgtgcctac    180
catggtgacc acgggtgacg gggaatcagg gttcgattcc ggagagggag cctgagaaac    240
ggctaccaca tccaaggaag gcagcaggcg cgcaaattac ccactcccga cccggggagg    300
tagtgacgaa aaataacaat acaggactct ttcgaggccc tgtaattgga atgagtccac    360
tttaaatcct ttaagcag                                                 378
```

<210> SEQ ID NO 10
<211> LENGTH: 378
<212> TYPE: DNA
<213> ORGANISM: Mus musculus

<400> SEQUENCE: 10

```
gatccattgg agggcaagtc tggtgccagc agccgcggta attccagctc caatagcgta    60
tattaaagtt gctgcagtta aaaagctcgt agttggatct tgggagcggg cgggcggtcc   120
gccgcgaggc gagtcaccgc ccgtcccgc ccttgcctc tcggcgcccc ctcgatgctc    180
ttagctgagt tgtcccgcgg ggcccgaagc gtttactttg aaaaaattag agttgtttca    240
aagcaggccc gagccgcctg gataccgcca gctaggaaat aatggaatag gaccgcggtt    300
cctattttgt ttggttttcg gaactgagcc catgattaag ggaaacggcc ggggcattc    360
ccttattgcg cccccta                                                  378
```

<210> SEQ ID NO 11
<211> LENGTH: 719
<212> TYPE: DNA
<213> ORGANISM: Mus musculus

<400> SEQUENCE: 11

```
ggatctttcc cgctccccgt tcctcccggc ccctccaccc gcgcgtctcc cccttctttt    60
tccctctcc ggaggggggg gaggtggggg gcgcgtgggcg gggtcggggg tgggtcggc   120
gggggaccgc ccccggccgg caaaaggccg ccgccgggcg cacttcaacc gtagcggtgc    180
gccgcgaccg gctacgagac ggctgggaag gcccgacggg gaatgtggct cgggggggc    240
ggcgcgtctc agggcgcgcc gaaccacctc accccgagtg ttacagccct ccggccgcgc    300
tttcgcggaa tccgggggcc gaggggaagc ccgatacccg tcgccgcgct tttcccctcc    360
ccccgtccgc ctcccgggcg ggcgtggggg tgggggccgg gccgcccctc ccacgcccgt    420
ggtttctctc tctcccggtc tcggccggtt tgggggggg agcccggttg ggggcggggc    480
ggactgtcct cagtgcgccc cgggcgtcgt cgcgccgtcg ggccggggg gttctctcgg    540
tcacgccgcc cccgacgaag ccgagcgcac gggtcggcg gcgatgtcgg ctacccaccc    600
gacccgtctt gaaacacgga ccaaggagtc taacgcgtgc gcgagtcagg ggctcgcacg    660
aaagccgccg tggcgcaatg aaggtgaagg gccccgtccg ggggcccgag gtgggatcc    719
```

<210> SEQ ID NO 12

<211> LENGTH: 685
<212> TYPE: DNA
<213> ORGANISM: Mus musculus

<400> SEQUENCE: 12

| | | | | | |
|---|---|---|---|---|---|
| cgaggcctct | ccagtccgcc | gagggcgcac | caccggcccg | tctcgcccgc | cgcgtcgggg | 60 |
| aggtggagca | cgagcgtacg | cgttaggacc | cgaaagatgg | tgaactatgc | ctgggcaggg | 120 |
| cgaagccaga | ggaaactctg | gtggaggtcc | gtagcggtcc | tgacgtgcaa | atcggtcgtc | 180 |
| cgacctgggt | ataggggcga | agactaatc | gaaccatcta | gtagctggtt | ccctccgaag | 240 |
| tttccctcag | gatagctggc | gctctcgcaa | ccttcggaag | cagttttatc | cgggtaaagg | 300 |
| cggaatggat | taggaggtct | tggggccgga | acgatctca | actatttct | caaactttaa | 360 |
| atgggtaagg | aagcccggct | cgctggcgtg | gagccgggcg | tggaatgcga | gtgcctagtg | 420 |
| ggccactttt | ggtaagcaga | actggcgctg | cgggatgaac | cgaacgccgg | gttaaggcgc | 480 |
| ccgatgccga | cgctcatcag | accccagaaa | aggtgttggt | tgatatagac | agcaggacgg | 540 |
| tggccatgga | agtcggaatc | cgctaaggag | tgtgtaacaa | ctcacctgcc | gaatcaacta | 600 |
| gccctgaaaa | tggatggcgc | tggagcgtcg | ggcccatacc | cggccgtcgc | cggcagtcgg | 660 |
| aacgggacgg | gacgggagcg | gccgc | | | | 685 |

<210> SEQ ID NO 13
<211> LENGTH: 5162
<212> TYPE: DNA
<213> ORGANISM: Artificial Sequence
<220> FEATURE:
<223> OTHER INFORMATION: Chimeric bacterial plasmid

<400> SEQUENCE: 13

| | | | | | |
|---|---|---|---|---|---|
| gacggatcgg | gagatctccc | gatcccctat | ggtcgactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacgggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggac | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acgtgtggag | gtctatataa | gcagagctct | ctggctaact | agagaaccca | 840 |
| ctgcttactg | gcttatcgaa | attaatacga | ctcactatag | ggagacccaa | gcttggtacc | 900 |
| gagctcggat | cgatatctgc | ggccgcgtcg | acggaattca | gtggatccac | tagtaacggc | 960 |
| cgccagtgtg | ctggaattaa | ttcgctgtct | gcgagggcca | gctgttgggg | tgagtactcc | 1020 |
| ctctcaaaag | cgggcatgac | ttctgcgcta | agattgtcag | tttccaaaaa | cgaggaggat | 1080 |
| ttgatattca | cctggcccgc | ggtgatgcct | ttgagggtgg | ccgcgtccat | ctggtcagaa | 1140 |
| aagacaatct | ttttgttgtc | aagcttgagg | tgtggcaggc | ttgagatctg | gccatacact | 1200 |

-continued

```
tgagtgacaa tgacatccac tttgcctttc tctccacagg tgtccactcc caggtccaac    1260
tgcaggtcga gcatgcatct agggcggcca attccgcccc tctccctccc cccccctaa    1320
cgttactggc cgaagccgct tggaataagg ccggtgtgcg tttgtctata tgtgattttc    1380
caccatattg ccgtcttttg caatgtgag ggcccggaaa cctggccctg tcttcttgac     1440
gagcattcct aggggtcttt ccctctcgc caaaggaatg caaggtctgt tgaatgtcgt     1500
gaaggaagca gttcctctgg aagcttcttg aagacaaaca acgtctgtag cgaccctttg    1560
caggcagcgg aaccccccac ctggcgacag gtgcctctgc ggccaaaagc cacgtgtata    1620
agatacacct gcaaaggcgg cacaacccca gtgccacgtt gtgagttgga tagttgtgga    1680
aagagtcaaa tggctctcct caagcgtatt caacaagggg ctgaaggatg cccagaaggt    1740
accccattgt atgggatctg atctggggcc tcggtgcaca tgctttacat gtgtttagtc    1800
gaggttaaaa aaacgtctag gccccccgaa ccacggggac gtggttttcc tttgaaaaac    1860
acgatgataa gcttgccaca acccgggatc caccggtcgc caccatggtg agcaagggcg    1920
aggagctgtt caccggggtg gtgcccatcc tggtcgagct ggacggcgac gtaaacggcc    1980
acaagttcag cgtgtccggc gagggcgagg gcgatgccac ctacggcaag ctgaccctga    2040
agttcatctg caccaccggc aagctgcccg tgcctggcc caccctcgtg accaccctga    2100
cctacggcgt gcagtgcttc agccgctacc ccgaccacat gaagcagcac gacttcttca    2160
agtccgccat gcccgaaggc tacgtccagg agcgcaccat cttcttcaag gacgacggca    2220
actacaagac ccgcgccgag gtgaagttcg agggcgacac cctggtgaac cgcatcgagc    2280
tgaagggcat cgacttcaag gaggacggca acatcctggg gcacaagctg gagtacaact    2340
acaacagcca caacgtctat atcatggccg acaagcagaa gaacggcatc aaggtgaact    2400
tcaagatccg ccacaacatc gaggacggca gcgtgcagct cgccgaccac taccagcaga    2460
acacccccat cggcgacggc cccgtgctgc tgcccgacaa ccactacctg agcacccagt    2520
ccgccctgag caaagacccc aacgagaagc gcgatcacat ggtcctgctg gagttcgtga    2580
ccgccgccgg gatcactctc ggcatggacg agctgtacaa gtaaagcggc cctagagctc    2640
gctgatcagc ctcgactgtg cctctagttg ccagccatct gttgtttgcc cctcccccgt    2700
gccttccttg accctggaag gtgccactcc cactgtcctt tcctaataaa atgaggaaat    2760
tgcatcgcat tgtctgagta ggtgtcattc tattctgggg ggtggggtgg ggcaggacag    2820
caagggggag gattggaag acaatagcag gcatgctggg gatgcggtgg gctctatggc     2880
ttctgaggcg gaaagaacca gctggggctc gagtgcattc tagttgtggt ttgtccaaac    2940
tcatcaatgt atcttatcat gtctgtatac cgtcgacctc tagctagagc ttggcgtaat    3000
catggtcata gctgtttcct gtgtgaaatt gttatccgct cacaattcca cacaacatac    3060
gagccggaag cataaagtgt aaagcctggg gtgcctaatg agtgagctaa ctcacattaa    3120
ttgcgttgcg ctcactgccc gctttccagt cgggaaacct gtcgtgccag ctgcattaat    3180
gaatcggcca acgcgcgggg agaggcggtt tgcgtattgg gcgctcttcc gcttcctcgc    3240
tcactgactc gctgcgctcg gtcgttcggc tgcggcgagc ggtatcagct cactcaaagg    3300
cggtaatacg gttatccaca gaatcagggg ataacgcagg aaagaacatg tgagcaaaag    3360
gccagcaaaa ggccaggaac cgtaaaaagg ccgcgttgct ggcgtttttc cataggctcc    3420
gcccccctga cgagcatcac aaaaatcgac gctcaagtca gaggtggcga aacccgacag    3480
gactataaag ataccaggcg tttccccctg gaagctccct cgtgcgctct cctgttccga    3540
```

-continued

```
ccctgccgct taccggatac ctgtccgcct ttctcccttc gggaagcgtg gcgctttctc    3600
aatgctcacg ctgtaggtat ctcagttcgg tgtaggtcgt tcgctccaag ctgggctgtg    3660
tgcacgaacc ccccgttcag cccgaccgct gcgccttatc cggtaactat cgtcttgagt    3720
ccaacccggt aagacacgac ttatcgccac tggcagcagc cactggtaac aggattagca    3780
gagcgaggta tgtaggcggt gctacagagt tcttgaagtg gtggcctaac tacggctaca    3840
ctagaaggac agtatttggt atctgcgctc tgctgaagcc agttaccttc ggaaaaagag    3900
ttggtagctc ttgatccggc aaacaaacca ccgctggtag cggtggtttt tttgtttgca    3960
agcagcagat tacgcgcaga aaaaaaggat ctcaagaaga tcctttgatc ttttctacgg    4020
ggtctgacgc tcagtggaac gaaaactcac gttaagggat tttggtcatg agattatcaa    4080
aaaggatctt cacctagatc cttttaaatt aaaaatgaag ttttaaatca atctaaagta    4140
tatatgagta aacttggtct gacagttacc aatgcttaat cagtgaggca cctatctcag    4200
cgatctgtct atttcgttca tccatagttg cctgactccc cgtcgtgtag ataactacga    4260
tacgggaggg cttaccatct ggccccagtg ctgcaatgat accgcgagac ccacgctcac    4320
cggctccaga tttatcagca ataaaccagc cagccggaag ggccgagcgc agaagtggtc    4380
ctgcaacttt atccgcctcc atccagtcta ttaattgttg ccgggaagct agagtaagta    4440
gttcgccagt taatagtttg cgcaacgttg ttgccattgc tacaggcatc gtggtgtcac    4500
gctcgtcgtt tggtatggct tcattcagct ccggttccca acgatcaagg cgagttacat    4560
gatcccccat gttgtgcaaa aaagcggtta gctccttcgg tcctccgatc gttgtcagaa    4620
gtaagttggc cgcagtgtta tcactcatgg ttatggcagc actgcataat tctcttactg    4680
tcatgccatc cgtaagatgc ttttctgtga ctggtgagta ctcaaccaag tcattctgag    4740
aatagtgtat gcggcgaccg agttgctctt gcccggcgtc aatacgggat aataccgcgc    4800
cacatagcag aactttaaaa gtgctcatca ttggaaaacg ttcttcgggg cgaaaactct    4860
caaggatctt accgctgttg agatccagtt cgatgtaacc cactcgtgca cccaactgat    4920
cttcagcatc ttttactttc accagcgttt ctgggtgagc aaaaacagga aggcaaaatg    4980
ccgcaaaaaa gggaataagg gcgacacgga aatgttgaat actcatactc ttcctttttc    5040
aatattattg aagcatttat cagggttatt gtctcatgag cggatacata tttgaatgta    5100
tttagaaaaa taaacaaata ggggttccgc gcacatttcc ccgaaaagtg ccacctgacg    5160
tc                                                                    5162
```